United States Patent
Jung et al.

(10) Patent No.: US 9,680,107 B2
(45) Date of Patent: Jun. 13, 2017

(54) COMPOUND AND ORGANIC ELECTRONIC DEVICE COMPRISING THE COMPOUND

(75) Inventors: Joon Ho Jung, Hwaseong-si (KR); Jeong Og Choi, Seoul (KR); Oh Kwan Kwon, Anyang-si (KR); Ah Reum Hwang, Seoul (KR)

(73) Assignee: LMS Co., Ltd., Pyeongtaek-si (KR)

( * ) Notice: Subject to any disclaimer, the term of this patent is extended or adjusted under 35 U.S.C. 154(b) by 750 days.

(21) Appl. No.: 14/119,317

(22) PCT Filed: May 25, 2012

(86) PCT No.: PCT/KR2012/004188
§ 371 (c)(1),
(2), (4) Date: Apr. 10, 2014

(87) PCT Pub. No.: WO2012/161554
PCT Pub. Date: Nov. 29, 2012

(65) Prior Publication Data
US 2014/0203251 A1 Jul. 24, 2014

(30) Foreign Application Priority Data
May 25, 2011 (KR) .......... 10-2011-0049399

(51) Int. Cl.
| | | |
|---|---|---|
| *H01L 51/54* | (2006.01) | |
| *C09K 11/06* | (2006.01) | |
| *H01L 51/00* | (2006.01) | |
| *C07D 209/82* | (2006.01) | |
| *H01L 51/50* | (2006.01) | |

(52) U.S. Cl.
CPC ........ *H01L 51/0058* (2013.01); *C07D 209/82* (2013.01); *H01L 51/006* (2013.01); *H01L 51/0061* (2013.01); *H01L 51/0068* (2013.01); *H01L 51/0072* (2013.01); *H01L 51/008* (2013.01); *H01L 51/5056* (2013.01); *H01L 51/5088* (2013.01)

(58) Field of Classification Search
CPC .. C07D 209/82; C07D 209/86; C07D 209/88; H01L 51/0032; H01L 51/005; H01L 51/0051; H01L 51/0059; H01L 51/0058; H01L 51/006; H01L 51/0061; H01L 51/0062; H01L 51/0068; H01L 51/0071; H01L 51/0072; H01L 51/0079; H01L 51/008; H01L 51/50; H01L 51/5056; H01L 51/506; H01L 51/5064
USPC ....... 428/690, 691, 917, 411.4, 336; 427/58, 427/66; 313/500–512; 257/40, 88–104, 257/E51.001–E51.052; 252/301.16–301.35; 548/440, 414; 564/16, 8
See application file for complete search history.

(56) References Cited

U.S. PATENT DOCUMENTS

| | | |
|---|---|---|
| 2005/0225235 A1 | 10/2005 | Kim et al. |
| 2005/0274961 A1* | 12/2005 | Iou ............... H01L 51/5088 257/82 |
| 2007/0090756 A1* | 4/2007 | Okada ............ H01L 51/5016 313/506 |
| 2007/0141390 A1 | 6/2007 | Coggan et al. |

FOREIGN PATENT DOCUMENTS

| | | | |
|---|---|---|---|
| JP | 860144 A | | 3/1996 |
| JP | 11185965 A | | 7/1999 |
| JP | 2009170813 A | * | 7/2009 |
| JP | 201097964 A | | 4/2010 |
| KR | 1020050118098 A | | 12/2005 |
| KR | 1020060051622 A | | 5/2006 |
| KR | 1020070067611 A | | 6/2007 |

OTHER PUBLICATIONS

Machine translation of JP2009-170813. Date of publication: Jul. 30, 2009.*
Machine translation of JP11-185965. Date of publication: Jul. 9, 1999.*

* cited by examiner

*Primary Examiner* — Andrew K Bohaty
(74) *Attorney, Agent, or Firm* — The Webb Law Firm

(57) ABSTRACT

Provided are a novel compound and an organic electronic device (OED) including the same. The novel compound has better hole injection and hole transport properties than a conventional material, and thus may enhance thermal stability and efficiency when used as a material for a hole injection or hole transport layer of the OED.

13 Claims, 2 Drawing Sheets

COMPOUND AND ORGANIC ELECTRONIC DEVICE COMPRISING THE COMPOUND

CROSS REFERENCE TO RELATED APPLICATION

This application is the United States national phase of International Application No. PCT/KR2012/004188 filed May 25, 2012 and claims priority to and the benefit of Korean Patent Application No. 2011-0049399, filed May 25, 2011, the disclosures of which are incorporated herein by reference in their entirety.

BACKGROUND

1. Field of the Invention

The present invention relates to a novel compound and an organic electronic device (OED) including the same, and particularly, to a novel compound used in an emitting device of a display device and an OED including the same.

2. Discussion of Related Art

An OED refers to an emitting device using an electroluminescent phenomenon in which light is emitted when a current flows through a light emitting organic compound. The OED can be manufactured without a backlight, is flexible, and is applicable in a variety of industrial fields.

However, heat applied from an external environment, heat generated inside of the OED, or an electric field applied to the OED may have an adverse influence on the performance of the OED since an interface between an electrode and an organic layer is unstable. In addition, while holes are provided from the electrode to an emitting layer, a driving voltage of the OED may be increased due to an energy barrier present at an interface between stacked components. Accordingly, it is important to stabilize the interface between layers of the stacked components and easily inject the holes by minimizing the energy barrier in the process of injecting the holes into the emitting layer from the electrode.

SUMMARY OF THE INVENTION

1. Technical Problem

The present invention is directed to providing a novel compound, which can enhance hole injection and transport capabilities, decrease consumption power, and enhance emitting efficiency of an emitting device.

The present invention is also directed to providing an OED including the compound.

2. Technical Solution

One aspect of the present invention provides a compound represented by Formula 1.

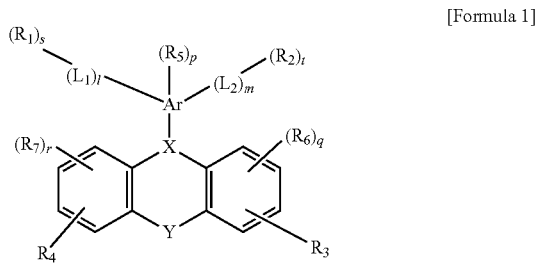

[Formula 1]

In Formula 1, X is selected from N, P, P(=O) and B, Y is a single bond or carbon, Ar is a $C_6$-$C_{50}$ arylene group, $L_1$ and $L_2$ are each independently a single bond, a $C_6$-$C_{50}$ arylene group, or a $C_4$-$C_{50}$ heteroarylene group, l and m are each independently 0 or 1, s and t are each independently 1 or 2, and $R_1$ and $R_2$ are each independently a $C_6$-$C_{50}$ aryl group, a $C_4$-$C_{50}$ heteroaryl group, or —N($R_8$)($R_9$), in which $R_8$ and $R_9$ are each independently a $C_6$-$C_{50}$ aryl group or a $C_4$-$C_{50}$ heteroaryl group. In the definition of $L_1$, $L_2$, $R_1$, $R_2$, $R_8$, and $R_9$, the $C_6$-$C_{50}$ aryl group and $C_4$-$C_{50}$ heteroaryl group may be each independently unsubstituted or substituted by at least one substituent selected from the group consisting of a $C_1$-$C_6$ alkyl group, a $C_1$-$C_6$ alkoxy group, a $C_6$-$C_{50}$ aryl group, a $C_4$-$C_{50}$ heteroaryl group, and —N($R_{10}$)($R_{11}$), in which $R_{10}$ and $R_{11}$ are each independently a $C_6$-$C_{50}$ aryl group unsubstituted or substituted by a $C_6$-$C_{30}$ arylamino group, or a $C_4$-$C_{50}$ heteroaryl group unsubstituted or substituted by a $C_6$-$C_{30}$ arylamino group, $R_3$ and $R_4$ are each independently hydrogen, or a $C_6$-$C_{50}$ aryl group unsubstituted or substituted by a $C_1$-$C_{12}$ alkyl group or a $C_6$-$C_{12}$ aryl group, and p, q, and r are each independently an integer of 0 to 3. When p, q, and r are each independently an integer of 1 or more, $R_5$, $R_6$, and $R_7$ are each independently hydrogen, a $C_1$-$C_{12}$ alkyl group, a $C_1$-$C_{12}$ alkoxy group, or a cyano group.

In addition, the present invention provides an OED including the compound of Formula 1 and an electronic system.

3. Effect of the Invention

According to the present invention, a novel compound and an OED including the same are provided. The novel compound can enhance hole injection and transport capabilities in the OED, power efficiency, and a lifetime of the device. Such an OED can be effectively applied to various kinds of electronic systems.

DETAILED DESCRIPTION OF EXEMPLARY EMBODIMENTS

Figure 1:
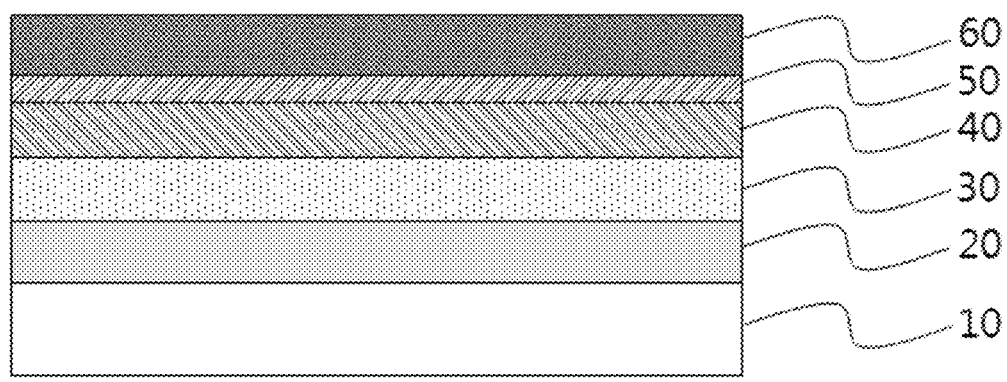
FIGS. 1, 2, and 3 are schematic diagrams of an OED structure including an organic layer containing a compound according to an exemplary embodiment of the present invention.

Hereinafter, a novel compound according to the present invention will be explained, and an OED including the novel compound will be explained with reference to the accompanying drawings.

The compound according to the present invention is represented by Formula 1.

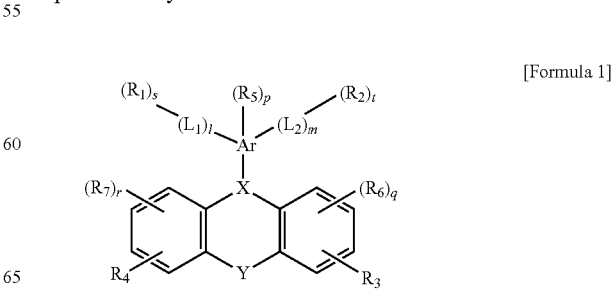

[Formula 1]

In Formula 1, X is selected from N, P, P(=O) and B, Y is a single bond or carbon, Ar is a $C_6$-$C_{50}$ arylene group, $L_1$ and $L_2$ are each independently a single bond, a $C_6$-$C_{50}$ arylene group, or a $C_4$-$C_{50}$ heteroarylene group, l and m are each independently 0 or 1, s and t are each independently 1 or 2, and $R_1$ and $R_2$ are each independently a $C_6$-$C_{50}$ aryl group, a $C_4$-$C_{50}$ heteroaryl group, or —N($R_8$)($R_9$), in which $R_8$ and $R_9$ are each independently a $C_6$-$C_{50}$ aryl group or a $C_4$-$C_{50}$ heteroaryl group. In the definition of $L_1$, $L_2$, $R_1$, $R_2$, $R_8$, and $R_9$, the $C_6$-$C_{50}$ aryl group and $C_4$-$C_{50}$ heteroaryl group may be each independently unsubstituted or substituted by at least one substituent selected from the group consisting of a $C_1$-$C_6$ alkyl group, a $C_1$-$C_6$ alkoxy group, a $C_6$-$C_{50}$ aryl group, a $C_4$-$C_{50}$ heteroaryl group, and —N($R_{10}$)($R_{11}$), in which $R_{10}$ and $R_{11}$ are each independently a $C_6$-$C_{50}$ aryl group unsubstituted or substituted by a $C_6$-$C_{30}$ arylamino group, or a $C_4$-$C_{50}$ heteroaryl group unsubstituted or substituted by a $C_6$-$C_{30}$ arylamino group, $R_3$ and $R_4$ are each independently hydrogen, or a $C_6$-$C_{50}$ aryl group unsubstituted or substituted by a $C_1$-$C_{12}$ alkyl group or a $C_6$-$C_{12}$ aryl group, and p, q, and r are each independently an integer of 0 to 3. When p, q, and r are each independently an integer of 1 or more, $R_5$, $R_6$, and $R_7$ are each independently hydrogen, a $C_1$-$C_{12}$ alkyl group, a $C_1$-$C_{12}$ alkoxy group, or a cyano group.

In Formula 1, the aryl group refers to a monovalent substituent derived from an aromatic hydrocarbon. The aryl group may be a monocyclic, dicyclic, or tricyclic aromatic hydrocarbon ring, such as a phenyl group, an indenyl group, an 1-naphthyl group, a 2-naphthyl group, an azulenyl group, a heptalenyl group, a biphenyl group, an indacenyl group, an acenaphthyl group, a fluorenyl group, a phenalenyl group, a phenanthrenyl group, an anthracenyl group, a dihydropyrenyl group, a cyclopentacyclooctenyl group, or a benzocyclooctenyl group. Hereinafter, the aryl group refers to a monovalent substituent derived from an aromatic hydrocarbon, which is subsequently the same as described above. Accordingly, repetitive specific descriptions will be omitted.

In addition, in Formula 1, the arylene group represented as "Ar" refers to a trivalent or a tetravalent substituent derived from the aryl group described above. In addition, in Formula 1, the arylene group of $L_1$ and $L_2$ refers to a bivalent substituent derived from the aryl group described above. Hereinafter, the arylene group represented as "Ar" refers to a trivalent or a tetravalent substituent derived from an aryl group which is substantially the same as defined above, and when an arylene group used as a linker linked to "Ar" is included, the arylene group of L1 and L2 refers to a bivalent substituent derived from the aryl group described above. Accordingly, the repetitive specific descriptions will be omitted.

In Formula 1, the alkyl group refers to a substituent derived from a linear or branched saturated hydrocarbon. Specific examples of the alkyl group may include linear or branched alkyl groups such as a methyl group, an ethyl group, a n-propyl group, an iso-propyl group, a n-butyl group, an iso-butyl group, a sec-butyl group, a tert-butyl group, a n-pentyl group, an 1,1-dimethylpropyl group, an 1,2-dimethylpropyl group, a 2,2-dimethylpropyl group, an 1-ethylpropyl group, a 2-ethylpropyl group, a n-hexyl group, an 1-methyl-2-ethylpropyl group, an 1-ethyl-2-methylpropyl group, an 1,1,2-trimethylpropyl group, an 1-propyl group, an 1-methylbutyl group, a 2-methylbutyl group, an 1,1-dimethylbutyl group, an 1,2-dimethylbutyl group, a 2,2-dimethylbutyl group, an 1,3-dimethylbutyl group, a 2,3-dimethylbutyl group, a 2-ethylbutyl group, a 2-methylpentyl group, and a 3-methylpentyl group.

In one embodiment, in Formula 1, X may be N, Y may be a single bond, and Ar may be a $C_6$-$C_{30}$ arylene group. $L_1$ and $L_2$ are each independently a single bond or a $C_6$-$C_{30}$ arylene group, l and m are each independently 0 or 1, s and t are each independently 1 or 2, $R_1$ and $R_2$ are each independently a $C_6$-$C_{30}$ aryl group, a $C_4$-$C_{30}$ heteroaryl group, or —N($R_8$)($R_9$), in which $R_8$ and $R_9$ are each independently a $C_6$-$C_{30}$ aryl group or a $C_4$-$C_{30}$ heteroaryl group. In the definition of $R_8$ and $R_9$, the $C_6$-$C_{30}$ aryl group or the $C_4$-$C_{30}$ heteroaryl group may be each independently unsubstituted or substituted by at least one substituent selected from the group consisting of a $C_1$-$C_4$ alkyl group, a $C_1$-$C_4$ alkoxy group, a $C_6$-$C_{30}$ aryl group, a $C_4$-$C_{30}$ heteroaryl group, and —N($R_{10}$)($R_{11}$). Here, $R_{10}$ and $R_{11}$ are each independently a $C_6$-$C_{30}$ aryl group unsubstituted or substituted by a $C_6$-$C_{30}$ arylamino group, or a $C_4$-$C_{30}$ heteroaryl group unsubstituted or substituted by a $C_6$-$C_{30}$ arylamino group, and $R_3$ and $R_4$ are each independently hydrogen, or a $C_6$-$C_{30}$ aryl group unsubstituted or substituted by a $C_1$-$C_{12}$ alkyl group or a $C_6$-$C_{12}$ aryl group.

Here, in Formula 1, p, q, and r are each independently 0 or 1, and when p, q, and r are each independently 1, $R_5$, $R_6$, and $R_7$ are each independently hydrogen, a $C_1$-$C_{12}$ alkyl group, a $C_1$-$C_{12}$ alkoxy group, or a cyano group.

In another embodiment, in Formula 1, X may be N, Y may be a single bond, and Ar may be phenylene. $L_1$ and $L_2$ may be each independently a single bond, phenylene, or naphthylene, and l and m may be each independently 0 or 1. $R_1$ and $R_2$ may be each independently a phenyl group, a naphthyl group, a thiophenyl group, a furanyl group, a benzothiophenyl group, a benzofuranyl group, an indolyl group, a carbazolyl group, a dibenzothiophenyl group, a dibenzofuranyl group, or —N($R_8$)($R_9$). Here, $R_8$ and $R_9$ are each independently a phenyl group, a naphthyl group, a thiophenyl group, a furanyl group, a benzothiophenyl group, a benzofuranyl group, an indolyl group, a carbazolyl group, a dibenzothiophenyl group, or a dibenzofuranyl group, and may be each independently unsubstituted or substituted by at least one substituent of a phenyl group, a naphthyl group, a thiophenyl group, a furanyl group, a benzothiophenyl group, a benzofuranyl group, an indolyl group, a carbazolyl group, a dibenzothiophenyl group, a dibenzofuranyl group, and —N($R_{10}$)($R_{11}$). Here, $R_{10}$ and $R_{11}$ may be each independently a phenyl group or a naphthyl group, $R_3$ and $R_4$ are each independently hydrogen, a phenyl group, a naphthyl group, a biphenyl group, a terphenyl group, or a fluorenyl group unsubstituted or substituted by a $C_1$-$C_{12}$ alkyl group or a $C_6$-$C_{12}$ aryl group. In one example, any one of $R_3$ and $R_4$ may be a fluorenyl group having a dimethyl group, in which two hydrogens are substituted by respective methyl groups.

In one example, the compound represented by Formula 1 may include a compound represented by Formula 2 or 3.

[Formula 2]

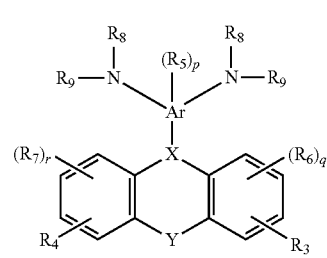

[Formula 3]

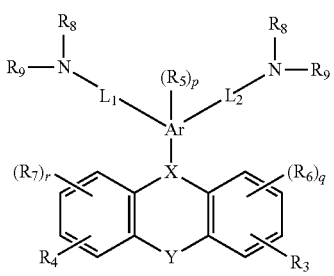

In both Formulas 2 and 3, the definition of each substituent is substantially the same as defined in Formula 1. Accordingly, the repetitive specific descriptions will be omitted.

In one example, in Formulas 2 and 3, X may be each independently selected from N, P, P(=O) and B, Y may be a single bond or carbon, Ar is a $C_6$-$C_{50}$ arylene group, and $L_1$ and $L_2$ may be each independently a single bond, a $C_6$-$C_{50}$ arylene group, or a $C_4$-$C_{50}$ heteroarylene group. $R_8$ and $R_9$ may be each independently a $C_6$-$C_{50}$ aryl group, or unsubstituted or substituted $C_4$-$C_{50}$ heteroaryl group. In the definition of $R_8$ and $R_9$, the $C_6$-$C_{50}$ aryl group and the $C_4$-$C_{50}$ heteroaryl group are each independently unsubstituted or substituted by at least one substituent selected from the group consisting of a $C_1$-$C_6$ alkyl group, a $C_1$-$C_6$ alkoxy group, a $C_6$-$C_{50}$ aryl group, a $C_4$-$C_{50}$ heteroaryl group, and —N($R_{10}$)($R_{11}$), $R_{10}$ and $R_{11}$ may be each independently a $C_6$-$C_{50}$ aryl group or a $C_4$-$C_{50}$ heteroaryl group; and $R_3$ and $R_4$ may be each independently hydrogen or a $C_6$-$C_{50}$ aryl group unsubstituted or substituted by a $C_1$-$C_{12}$ alkyl group or a $C_6$-$C_{12}$ aryl group. p, q, and r are each independently an integer of 0 to 3, and when p, q, and r are each independently an integer of 1 or more, each of $R_5$, $R_6$, and $R_7$ may be hydrogen, a $C_1$-$C_{12}$ alkyl group, a $C_1$-$C_{12}$ alkoxy group, or a cyano group.

In one embodiment, in Formulas 2 and 3, each independently, X may be N, Y may be a single bond, and Ar may be a $C_6$-$C_{30}$ arylene group. $L_1$ and $L_2$ may be each independently a single bond, a $C_6$-$C_{50}$ arylene group, or a $C_4$-$C_{50}$ heteroarylene group. $R_8$ and $R_9$ may be a $C_6$-$C_{30}$ aryl group or a $C_4$-$C_{30}$ heteroaryl group. $R_8$ and $R_9$ may be each independently unsubstituted or substituted by at least one substituent of a $C_6$-$C_{30}$ aryl group, a $C_4$-$C_{30}$ heteroaryl group, and —N($R_{10}$)($R_{11}$), in which $R_{10}$ and $R_{11}$ may be each independently a $C_6$-$C_{30}$ aryl group unsubstituted or substituted by a $C_6$-$C_{30}$ arylamino group. $R_3$ and $R_4$ may be each independently hydrogen, a phenyl group, a naphthyl group, a biphenyl group, a terphenyl group, or a fluorenyl group unsubstituted or substituted by a $C_1$-$C_{12}$ alkyl group or a $C_6$-$C_{12}$ aryl group; and $R_5$, $R_6$, and $R_7$ may be each independently hydrogen, a $C_1$-$C_{12}$ alkyl group, a $C_1$-$C_{12}$ alkoxy group, or a cyano group.

For example, specifically, the compounds represented by Formulas 2 and 3 may include compounds represented by Formulas 1-1 to 1-19.

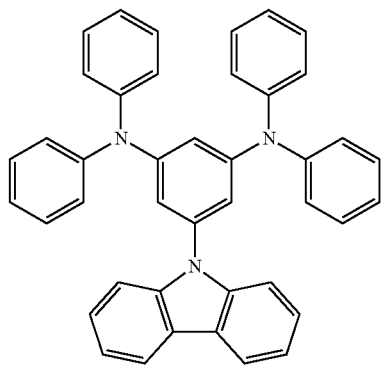

1-1

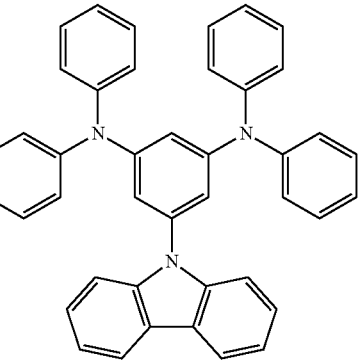

1-2

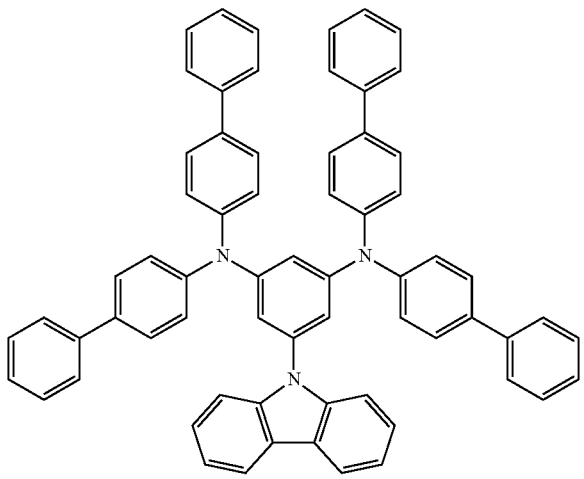

1-3

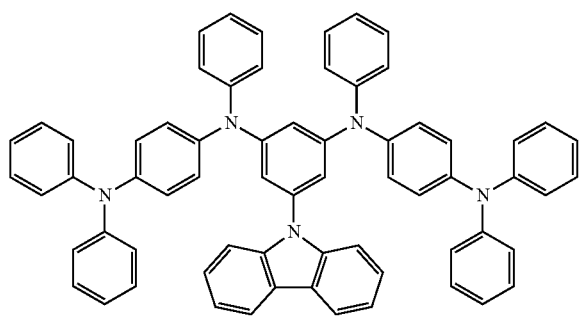

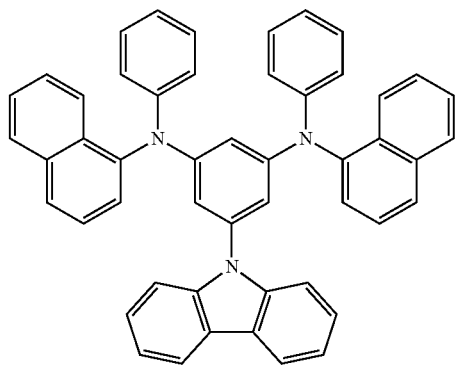

1-4

1-5
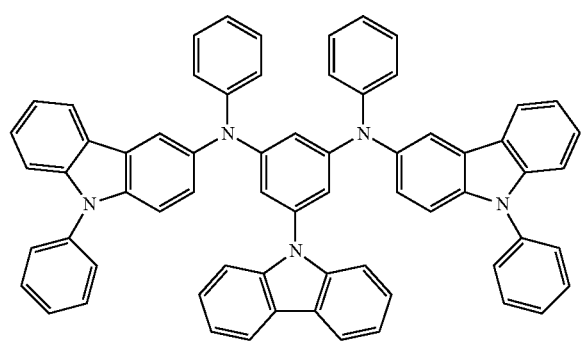
1-6
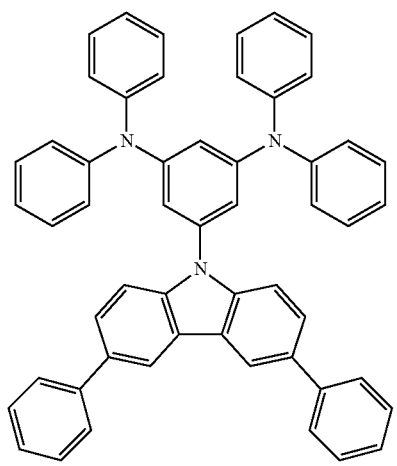
1-7
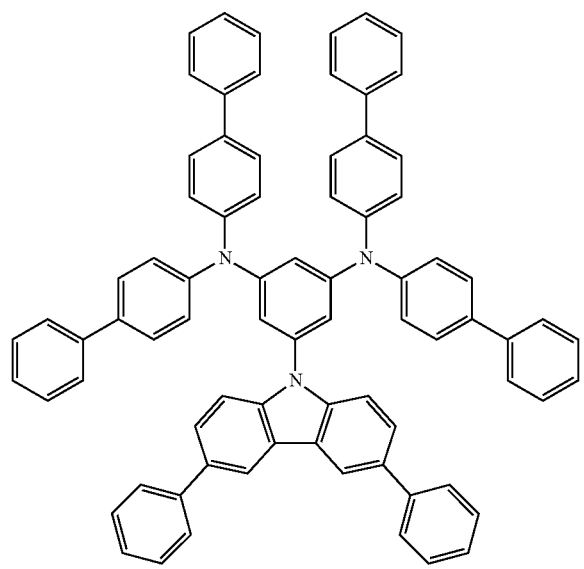
1-8
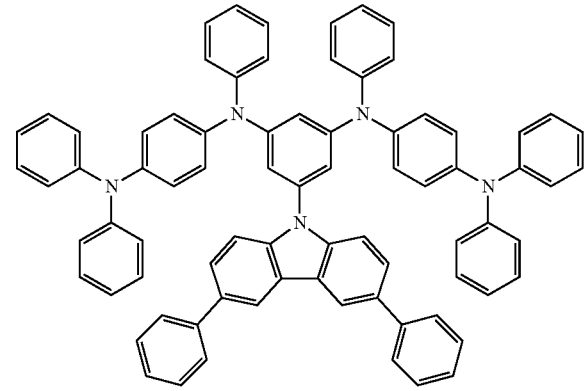
1-9
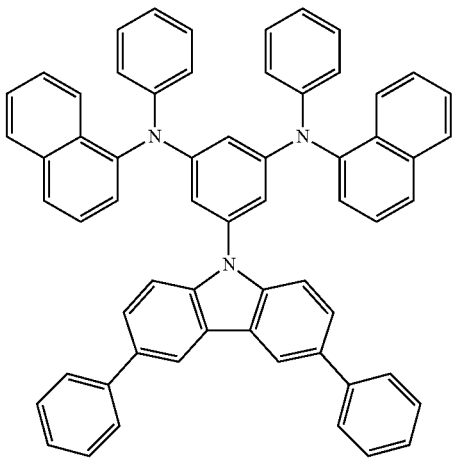
1-10
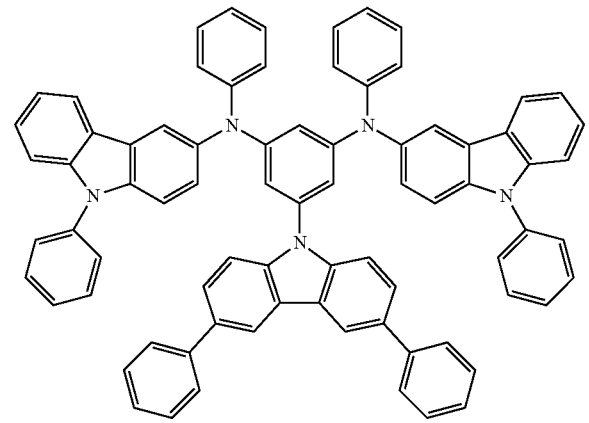

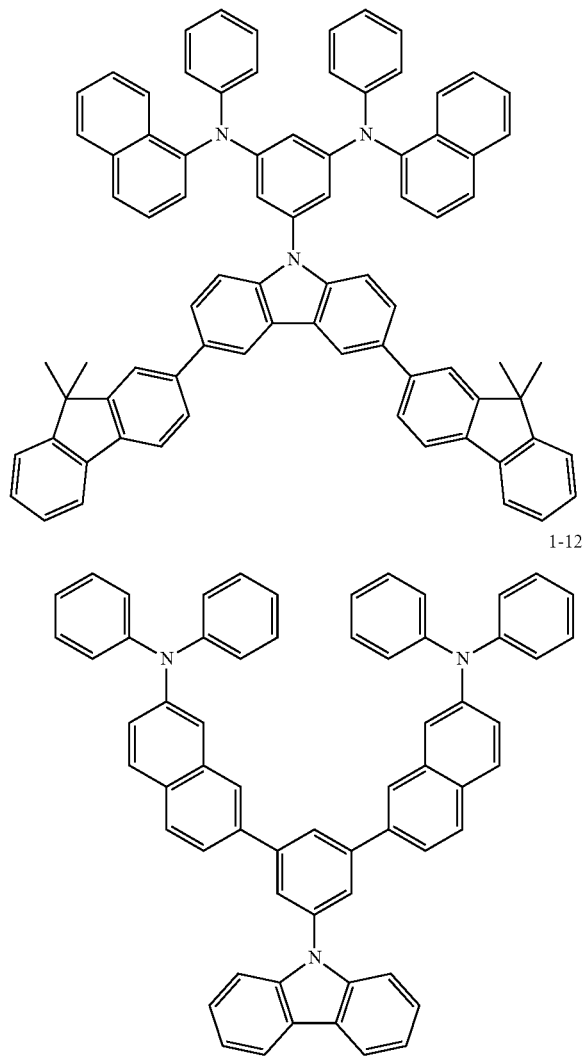
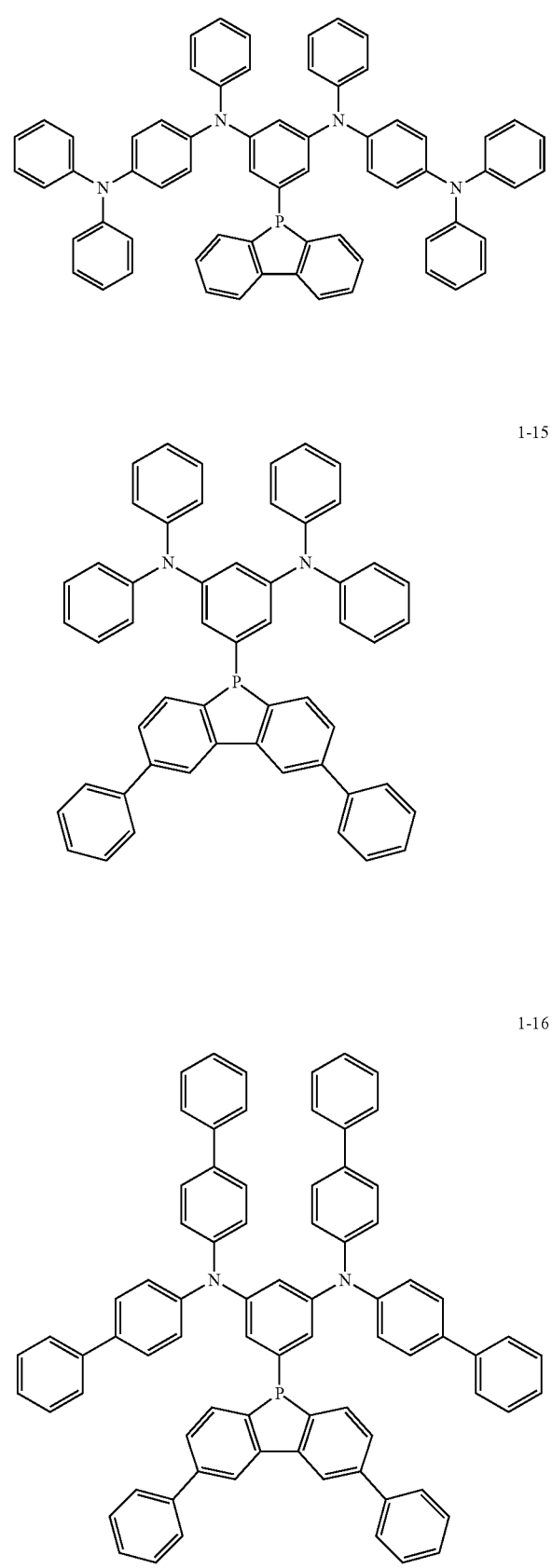

1-17

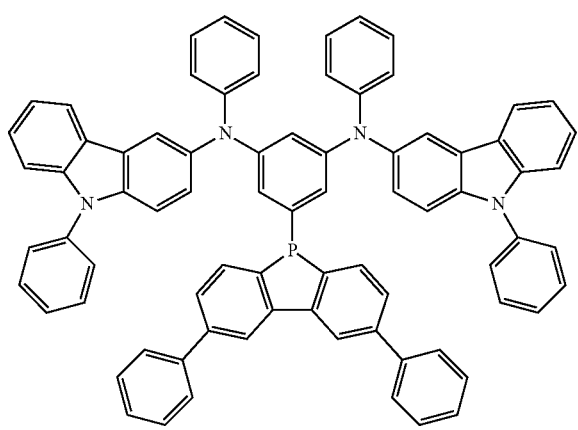

1-18

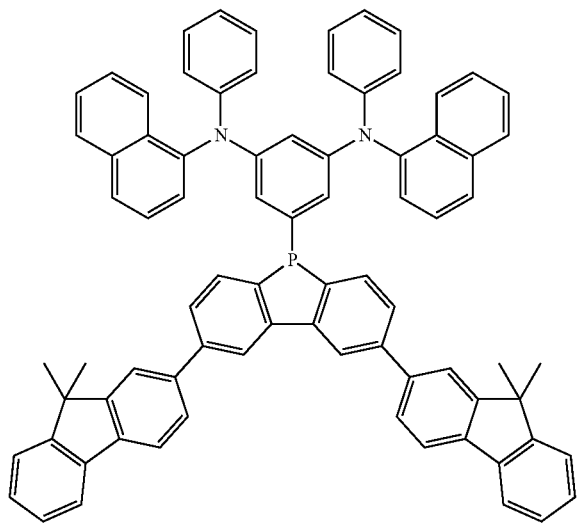

1-19

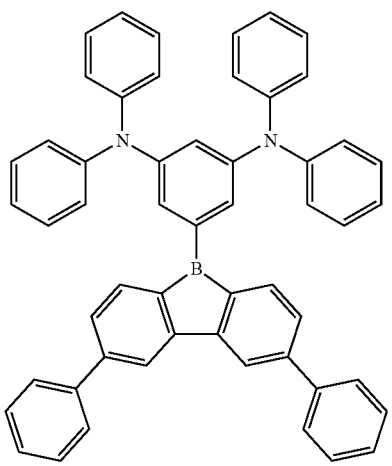

In one embodiment, Formula 1 may be represented by Formula 4.

[Formula 4]

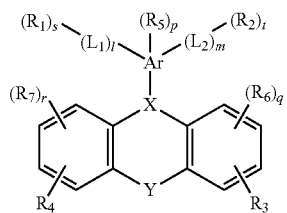

In Formula 4, X may be selected from N, P, P(=O) and B, Y may be a single bond or carbon, Ar may be a $C_6$-$C_{30}$ arylene group, $L_1$ and $L_2$ may be each independently a single bond or a $C_6$-$C_{30}$ arylene group, s and t may be each independently 1 or 2, $R_1$ and $R_2$ may be each independently a $C_6$-$C_{30}$ aryl group or a $C_4$-$C_{30}$ heteroaryl group, $R_3$ and $R_4$ may be each independently hydrogen, or a $C_6$-$C_{30}$ aryl group unsubstituted or substituted by a $C_1$-$C_{12}$ alkyl group or a $C_6$-$C_{12}$ aryl group, and $R_5$, $R_6$, and $R_7$ may be each independently hydrogen, a $C_1$-$C_{12}$ alkyl group, a $C_1$-$C_{12}$ alkoxy group, or a cyano group.

In one embodiment, in Formula 4, X may be N, Y may be a single bond or carbon, and Ar may be a $C_6$-$C_{30}$ arylene group. $L_1$ and $L_2$ may be each independently a single bond or a $C_6$-$C_{30}$ arylene group, and s and t may be each independently 1 or 2. $R_1$ and $R_2$ may be each independently a $C_6$-$C_{30}$ aryl group or a $C_4$-$C_{30}$ heteroaryl group. $R_3$ and $R_4$ may be each independently hydrogen, a phenyl group, a naphthyl group, a biphenyl group, a terphenyl group, or a fluorenyl group unsubstituted or substituted by a $C_1$-$C_{12}$ alkyl group or a $C_6$-$C_{12}$ aryl group, and $R_5$, $R_6$, and $R_7$ may be each independently hydrogen or a cyano group.

For example, the compound represented by Formula 4 may include at least one of the compounds represented by Formulas 4-1 to 4-4.

4-1

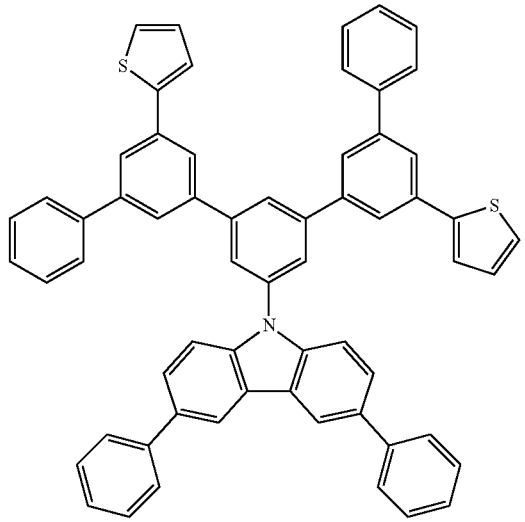

-continued

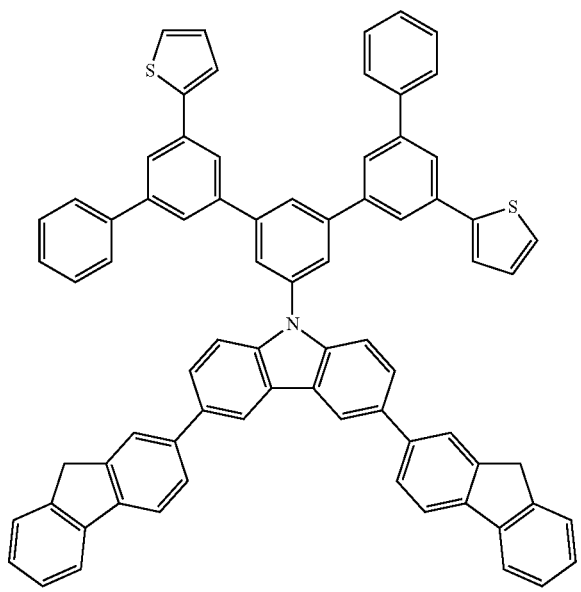
4-2

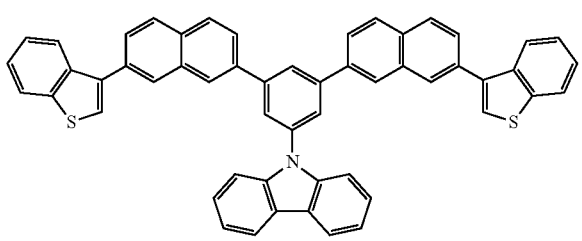
4-3

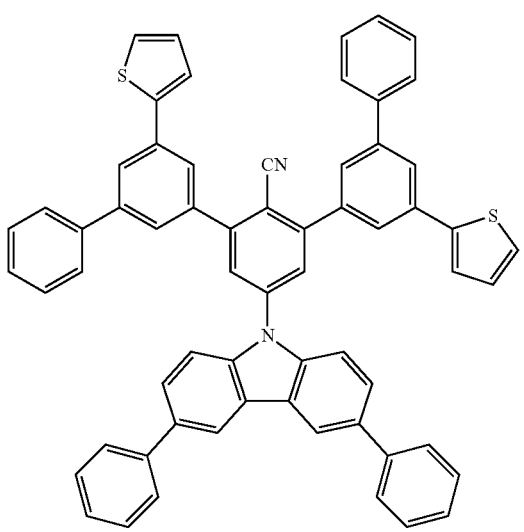
4-4

The present invention provides an OED including the compound described above.

In one embodiment, the OED may include a first electrode, a second electrode, and at least one organic layer including an emitting layer which is formed between the first electrode and the second electrode. The OED may also include a hole transport layer formed between the first electrode and the emitting layer, and containing a hole transport material. The hole transport material may be the compound described above based on the present invention.

In another embodiment, the OED may include a first electrode, a second electrode, and at least one organic layer including an emitting layer which is formed between the first electrode and the second electrode. The OED may further include a hole transport layer formed between the first electrode and the emitting layer and containing a hole transport material and a p-type dopant, and the hole transport material may be the compound described above based on the present invention.

The type of the p-type dopant is not particularly limited, and may include at least one of a p-type organic dopant and a p-type inorganic dopant.

A specific example of the p-type organic dopant may be any one of the compounds of Formulas 5 to 8, such as hexadecafluorophthalocyanine ($F_{16}CuPc$), 11,11,12,12-tetracyanonaphtho-2,6-quinodimethane (TNAP), 3,6-difluoro-2,5,7,7,8,8-hexacyano-quinodimethane ($F_2$-HCNQ), or tetracyanoquinodimethane (TCNQ), which may be used alone or in a combination of at least two thereof.

[Formula 5]

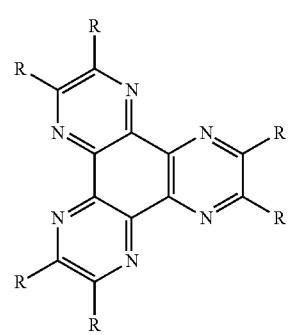

In Formula 5, R may be a cyano group, a sulfone group, a sulfoxide group, a sulfonamide group, a sulfonate group, a nitro group, or a trifluoromethyl group.

[Formula 6]

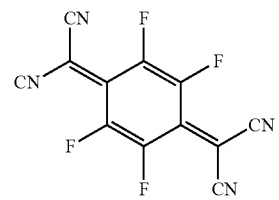

[Formula 7]

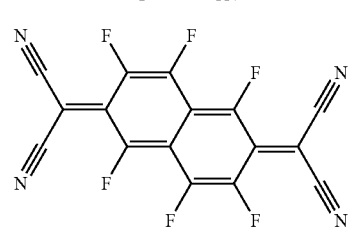

[Formula 8]

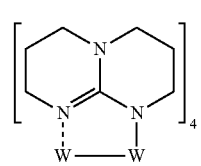

The p-type inorganic dopant may further include at least one of a metal oxide and a metal halide. A specific example of the p-type inorganic dopant may be $MoO_3$, $V_2O_5$, $WO_3$, $SnO_2$, ZnO, $MnO_2$, $CoO_2$, $ReO_3$, $TiO_2$, $FeCl_3$, $SbCl_5$, or $MgF_2$, which may be used alone or in a combination of at least two thereof.

A content of the p-type dopant doped into the hole transport layer may be 0.5 to 20 parts by weight with respect to 100 parts by weight of the hole transport material. Particularly, the content of the p-type dopant may be 0.5 to 20, 0.5 to 15, 0.5 to 5, 1 to 10, 1 to 5, 1.5 to 6, or 2 to 5 parts by weight with respect to 100 parts by weight of the hole transport material. In the above range, the physical properties of the hole transport material may not be degraded, the generation of excess current leakage may be prevented, and an energy barrier generated at an interface between two different layers adjacent to the hole transport layer may be effectively reduced.

In still another embodiment, the OED may include a first electrode, a second electrode, and at least one organic layer including an emitting layer which is formed between the first electrode and the second electrode. The OED may further include a first hole transport layer containing a hole transport material and a p-type dopant which is formed between the first electrode and the emitting layer, and a second hole transport layer containing a hole transport material. The hole transport materials contained in the first and second hole transport layers may be each independently the compound described above based on the present invention. For example, the first hole transport layer may have the same material as the second hole transport layer excluding a p-type dopant. In the present invention, as the components of the hole transport materials contained in the first hole transport layer and the second hole transport layer are the same, physiochemical defects which can be generated at an interface between hetero materials may be reduced, and thus holes can be easily injected into the emitting layer. In another aspect, when the first hole transport layer is formed of the same material as the second hole transport layer, the first hole transport layer and the second hole transport layer may be continuously formed in one chamber, and thus the manufacturing process becomes simple and the manufacturing time can be reduced. Furthermore, since the physical properties such as a glass transition temperature between adjacent layers become similar, durability of the device can be increased.

The first hole transport layer may have a variety of thicknesses in a range corresponding to a resonance length depending on the type of an OED.

In one example, the first hole transport layer may have a thickness of approximately 800 to 1500, 800 to 1000, 1000 to 1500, or 1100 to 1300 Å. In addition, the second hole transport layer may have a thickness of, but not particularly limited to, approximately 250 to 450 Å. For example, the second hole transport layer may have a thickness of approximately 250 to 400, 300 to 400, 250 to 300, or 300 to 400 Å.

In another example, the second hole transport layer may further include a p-type dopant. The p-type dopant doped into the second hole transport layer and the p-type dopant doped into the first hole transport layer may have different components, a different composition ratio though having the same components, or have different doping concentrations. On the other hand, the p-type dopant doped into the second hole transport layer and the p-type dopant doped into the first hole transport layer may have the same components, but different doping concentrations. For example, a content (P1) of the p-type dopant doped into the first hole transport layer and a content (P2) of the p-type dopant doped into the second hole transport layer may satisfy Equation 1.

$$P1/P2 \geq 1 \quad \text{[Equation 1]}$$

In Equation 1, P1 is a concentration of the doped p-type dopant with respect to 100 parts by weight of a hole transport material in the first hole transport layer, and P2 is a concentration of the doped p-type dopant with respect to 100 parts by weight of the hole transport material in the second hole transport layer.

For example, the concentration of the doped p-type dopant in the first hole transport layer may be 0.3 to 20, 1 to 15, 2 to 10, or 4 to 6 parts by weight based on 100 parts by weight of the hole transport material. In addition, the concentration of the doped p-type dopant in the second hole transport layer may be 0.3 to 20, 0.5 to 10, 1 to 8, or 2 to 4 parts by weight, based on 100 parts by weight of the hole transport material.

In addition, the p-type dopant doped into the first and/or second hole transport layer may be each independently at least one of the p-type organic and inorganic dopants. The description of the type of the p-type dopant is the same as the description above.

In yet another embodiment, the OED may further include a dopant layer formed between a first electrode and a hole transport layer and be formed of a p-type dopant. The dopant layer refers to a structure having one layer using a p-type dopant without a separate hole transport material. For example, the dopant layer may be formed using a material the same as or different from a p-type dopant included in a first hole transport layer. The dopant layer serves to increase mobility of the hole between the first electrode and the first hole transport layer. The dopant layer may have a thickness of, but not particularly limited to, for example, approximately 5 to 100, 10 to 70, 8 to 40, 10 to 30, 8 to 32, 8 to 12, 15 to 60, or 40 to 60 Å.

In yet another embodiment, the OED may further include at least one of a first blocking layer formed between a first electrode and an emitting layer to be in contact with the emitting layer and a second blocking layer formed between a second electrode and an emitting layer to be in contact with the emitting layer. For example, the first blocking layer may serve as an electron blocking layer (EBL), and the second blocking layer may serve as a hole blocking layer (HBL). The first and second blocking layers may be formed of various materials commercially available in the art without any limitations. The first blocking layer may serve to prevent the injection of electrons from the second electrode toward a hole transport material through the emitting layer. In addition, the second blocking layer may serve to prevent the injection of holes from the first electrode toward an electron transport material through the emitting layer.

The thicknesses of the first and second blocking layers may be each independently approximately 10 to 200 Å. For example, the thickness of the first blocking layer may be in the range of approximately 10 to 200, 20 to 200, 30 to 150, or 50 to 130 Å. The thickness of the second blocking layer may be in the range of approximately 10 to 200 Å. For example, the thickness of the second blocking layer may be in the range of approximately 10 to 200, 30 to 200, 50 to 150, or 50 to 130 Å. When the thicknesses of the first and second blocking layers are regulated to match a resonance length of an OED, emission efficiency may be further increased, and moreover, an exciton may be formed in the center of the emitting layer.

The present invention provides an electronic system including the above-described OED. The type of the electronic system is not particularly limited, and may be a lighting device, a display device, an organic solar cell, or an organic thin film transistor. For example, the display device may be an organic light emitting device (OLED).

Hereinafter, the present invention will be described in further detail with reference to the accompanying drawings. However, the present invention is not limited to a structure which will be described below.

Figure 2:
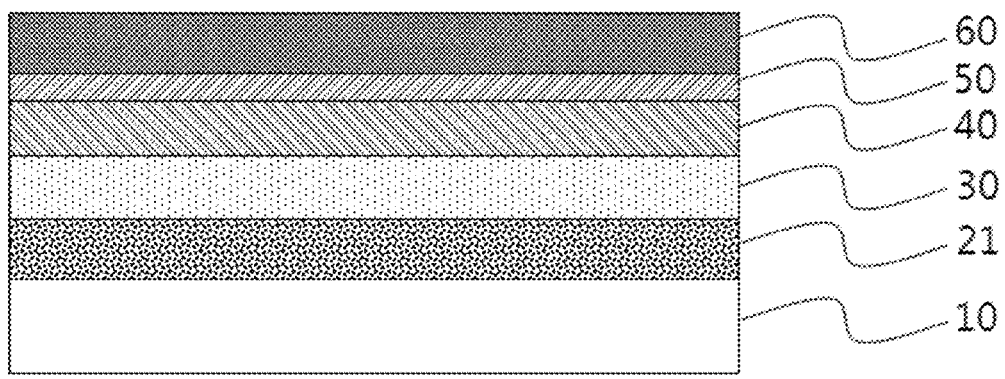
Figure 3:
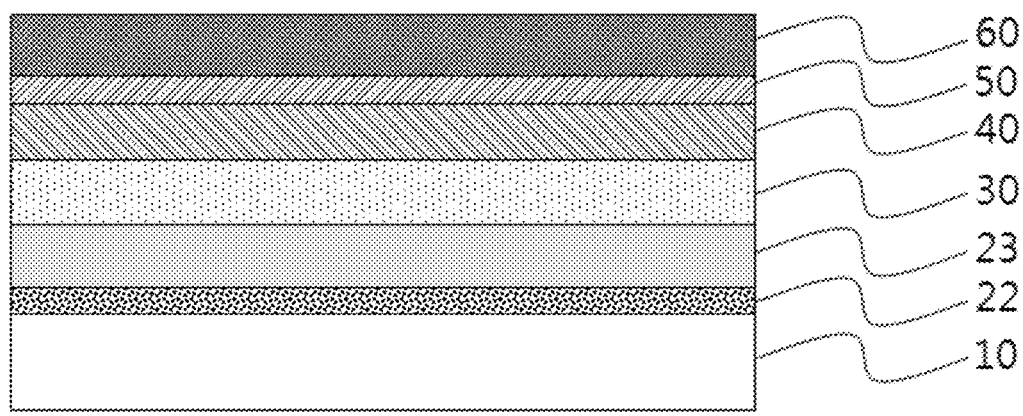

FIGS. 1, 2, and 3 are schematic diagrams of structures of an OED including an organic layer containing a compound based on an exemplary embodiment of the present invention.

Referring to FIG. 1, an OED includes a hole transport layer 20 formed on an ITO electrode 10 and containing a hole transport material. The OED may be formed by sequentially stacking an emitting layer 30, an electron transport layer 40, an electron injection layer 50, and an aluminum electrode 60 on the hole transport layer 20.

Referring to FIG. 2, an OED includes a hole transport layer 21 formed on an ITO electrode 10 and containing a hole transport material and a p-type dopant. A concentration of the p-type dopant may be regulated in various ranges from 0.3 to 20 parts by weight based on 100 parts by weight of the hole transport material of the hole transport layer 21. The OED may be formed by sequentially stacking an emitting layer 30, an electron transport layer 40, an electron injection layer 50, and an aluminum electrode 60 on the hole transport layer 21.

Referring to FIG. 3, an OED includes a hole transport layer formed on an ITO electrode 10 and containing a hole transport material. The hole transport layer includes a first hole transport layer 22 and a second hole transport layer 23. The first hole transport layer 22 further includes a p-type dopant, in addition to a hole transport material, and a concentration of the p-type dopant may be regulated variably within the range from 0.3 to 20 parts by weight based on 100 parts by weight of the hole transport material of the first hole transport layer 22. The second hole transport layer 23 contains a hole transport material, and in some cases, may further include a p-type dopant. Here, the second hole transport layer 23 may include a p-type dopant in a smaller amount than the first hole transport layer 22. The OED may be formed by sequentially stacking an emitting layer 30, an electron transport layer 40, an electron injection layer 50, and an aluminum electrode 60 on the first and second hole transport layers 22 and 23.

DETAILED DESCRIPTION OF EXEMPLARY EMBODIMENTS

Hereinafter, the present invention will be described in further detail with reference to the Examples based on the present invention, but the scope of the present invention is not limited to the following Examples.

Example 1 (Synthesis of Compound 1)

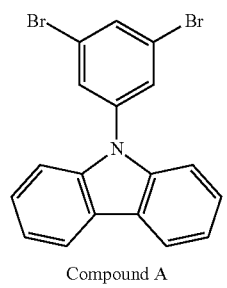

Compound A

+

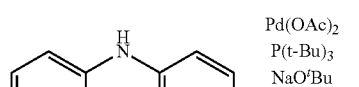

Compound J

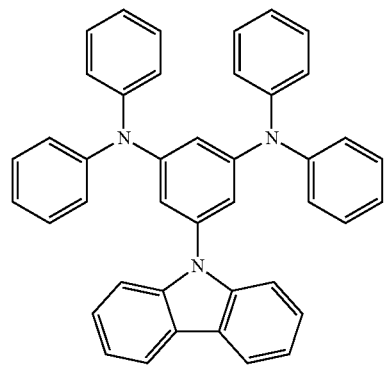

Compound 1

A 250 mL 3-neck round bottom flask was charged with nitrogen, and then a compound A which is 9-(3,5-dibromophenyl)-9H-carbazole (37.4 mmol, 15.0 g), a compound J which is diphenylamine (82.3 mmol, 13.9 g), palladium acetate (Pd(OAc)$_2$; 3.7 mmol, 0.8 g), sodium tert-butoxide (82.3 mmol, 7.9 g), 150 mL of o-xylene, and tri-tert-butylphosphine (7.4 mmol, 1.7 mL) were added thereto, and the resulting mixture was cooled from 130° C. to room temperature, stirred in 750 mL of methanol for 20 minutes, and filtered, thereby obtaining 21.2 g of a white solid, Compound 1 (yield: 98%).

MALDI-TOF: m/z=577.1692 (C$_{42}$H$_{31}$N$_3$=577.72)

1H-NMR (CDCl$_3$, 500 MHz) δ: 8.15 (d, J=7.74 Hz, 2H), 7.38 (d, J=3.74 Hz, 4H), 7.32 (t, J=7.95 Hz, 8H), 7.22-7.24 (m, 2H), 7.17 (d, J=7.69 Hz, 8H), 7.04 (t, J=7.35 Hz, 4H), 6.66 (s, 1H), 6.52 (d, J=1.87 Hz, 2H)

Example 2 (Synthesis of Compound 2)

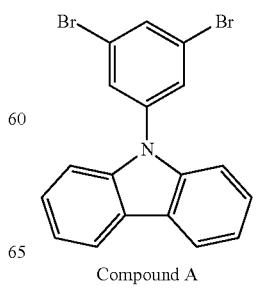

Compound A

+

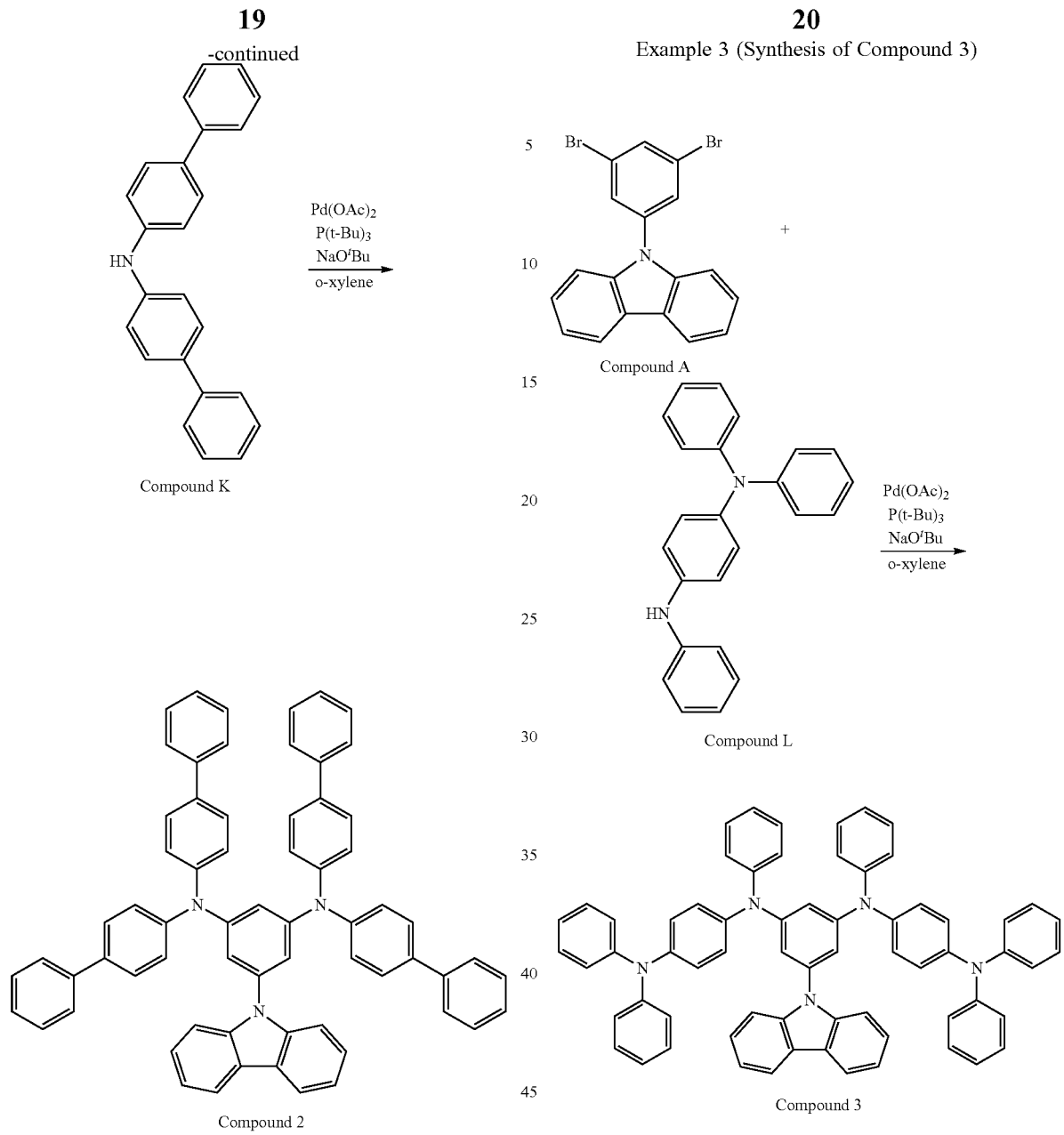

Example 3 (Synthesis of Compound 3)

A 250 mL 3-neck round bottom flask was charged with nitrogen, and then a compound A which is 9-(3,5-dibromophenyl)-9H-carbazole (34.9 mmol, 14.0 g), a compound K which is bis-biphenyl-4-yl-amine (69.8 mmol, 22.4 g), palladium acetate (Pd(OAc)$_2$; 1.8 mmol, 0.4 g), sodium tert-butoxide (76.8 mmol, 7.35 g), 70 mL of o-xylene, and tri-tert-butylphosphine (3.5 mmol, 0.8 mL) were added thereto, and the resulting mixture was heated at 130° C. for 4 hours. The solution of the mixture was cooled to room temperature, and 140 mL of tetrahydrofuran was added thereto. The solution of the mixture was stirred in 500 mL of methanol. The solution of the mixture was stirred for 30 minutes and filtered, thereby obtaining 29.0 g of a white solid, Compound 2 (yield: 94%).

MALDI-TOF: m/z=881.1052 ($C_{66}H_{47}N_3$=881.38)

1H-NMR (CDCl$_3$, 500 MHz) δ: 8.06 (d, J=7.5 Hz, 2H), 7.51 (d, J=6.5 Hz, 18H), 7.41-7.34 (m, 10H), 7.32-7.30 (m, 12H), 7.25-7.22 (m, 2H), 6.98 (t, J=1.5 Hz, 1H), 6.94 (d, J=2 Hz, 2H)

An 100 mL 3-neck round bottom flask was charged with nitrogen, and then a compound A which is 9-(3,5-dibromophenyl)-9H-carbazole (24.7 mmol, 9.9 g), a compound L which is (4-anilinophenyl)diphenylamine (54.3 mmol, 18.3 g), palladium acetate (Pd(OAc)$_2$; 2.5 mmol, 0.6 g), sodium tert-butoxide (54.3 mmol, 5.2 g), 50 mL of o-xylene, and tri-tert-butylphosphine (5.0 mmol, 1.2 mL) were added thereto, and the resulting mixture was heated at 130° C. for 6 hours. The solution of the mixture was cooled to room temperature, stirred in 750 mL of methanol for 20 minutes, and filtered, thereby obtaining 15.9 g of a white solid, Compound 3 (yield: 70%).

MALDI-TOF: m/z=911.2232 ($C_{66}H_{49}N_5$=912.13)

1H-NMR (CDCl$_3$, 500 MHz) δ: 8.19 (d, J=7.68 Hz, 2H), 7.41 (d, J=8.21 Hz, 2H), 7.36 (t, J=7.25 Hz, 2H), 7.31 (t, J=8.16 Hz, 4H), 7.26 (t, J=7.73 Hz, 10H), 7.20 (d, J=7.72 Hz, 4H), 7.14 (d, J=8.80 Hz, 4H), 6.94-7.06 (m, 18H), 6.62 (s, 1H), 6.50 (d, J=1.85 Hz, 2H)

Example 4 (Synthesis of Compound 4)

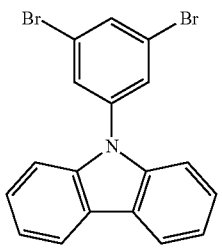
Compound A

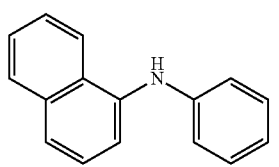
Compound M

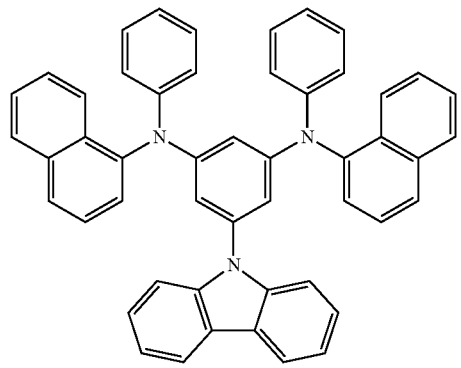
Compound 4

A 250 mL 3-neck round bottom flask was charged with nitrogen, and then a compound A which is 9-(3,5-dibromophenyl)-9H-carbazole (24.9 mmol, 10.0 g), a compound M which is N-phenyl-1-naphthylamine (49.9 mmol, 10.9 g), palladium acetate (Pd(OAc)$_2$; 1.2 mmol, 0.3 g), sodium tert-butoxide (50.0 mmol, 4.8 g), 100 mL of o-xylene, and tri-tert-butylphosphine (2.4 mmol, 0.6 mL) were added thereto, and the resulting mixture was heated at 130° C. for 3 hours. The solution of the mixture was cooled to room temperature, stirred in 500 mL of methanol for 20 minutes, and filtered, thereby obtaining 15.0 g of a solid, Compound 4 (yield: 88%).

MALDI-TOF: m/z=677.2076 (C$_{50}$H$_{35}$N$_3$=677.83)

1H-NMR (CDCl$_3$, 500 MHz) δ: 7.96-8.06 (m, 6H), 7.84 (d, J=7.80 Hz, 2H), 7.59 (t, J=8.16 Hz, 4H), 7.51 (t, J=7.73 Hz, 2H), 7.41 (d, J=7.72 Hz, 2H), 7.10-7.25 (m, 12H), 6.88-6.96 (m, 4H), 6.65 (s, 1H), 6.17 (d, J=1.85 Hz, 2H)

Example 5 (Synthesis of Compound 5)

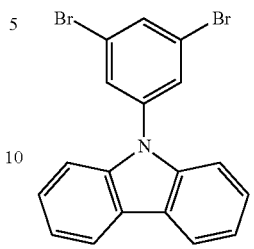
Compound A

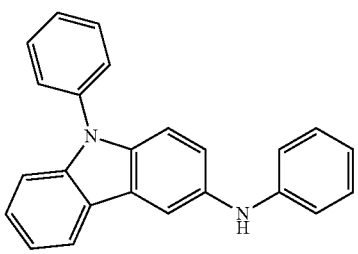
Compound N

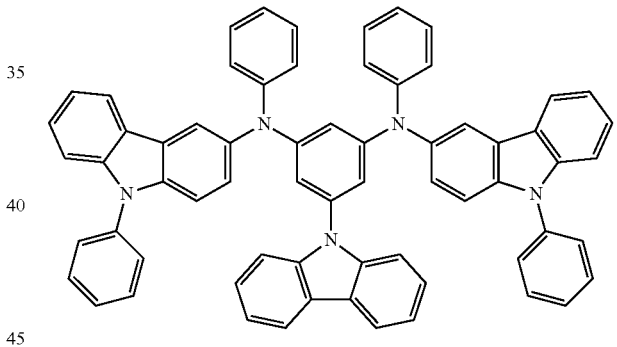
Compound 5

A 250 mL 3-neck round bottom flask was charged with nitrogen, and then a compound A which is 9-(3,5-dibromophenyl)-9H-carbazole (37.5 mmol, 15.0 g), a compound N which is 9H-phenylcarbazole-3-phenylamine (75.0 mmol, 25.0 g), palladium acetate (Pd(OAc)$_2$; 3.8 mmol, 0.8 g), sodium tert-butoxide (75.0 mmol, 7.2 g), 150 mL of o-xylene, and tri-tert-butylphosphine (7.6 mmol, 1.8 mL) were added thereto, and the resulting mixture was heated at 130° C. for 3 hours. The solution of the mixture was cooled to room temperature, stirred in 700 mL of methanol for 30 minutes, and filtered, thereby obtaining 13.6 g of a white solid, Compound 5 (yield: 40%).

MALDI-TOF: m/z=907.2235 (C$_{66}$H$_{45}$N$_5$=908.10)

1H-NMR (CDCl$_3$, 500 MHz) δ: 8.29 (d, J=7.68 Hz, 2H), 8.24 (s, 2H), 8.09 (d, J=7.77 Hz, 2H), 7.63 (t, J=7.60 Hz, 4H), 7.52 (d, J=7.65 Hz, 6H), 7.47 (d, J=8.26 Hz, 2H), 7.42 (t, J=7.77 Hz, 2H), 7.26-7.33 (m, 18H), 7.14 (t, J=7.42 Hz, 2H), 6.93~6.96 (m, 2H), 6.74 (s, 1H), 6.49 (d, J=1.87 Hz, 2H)

Example 6 (Synthesis of Compound 6)

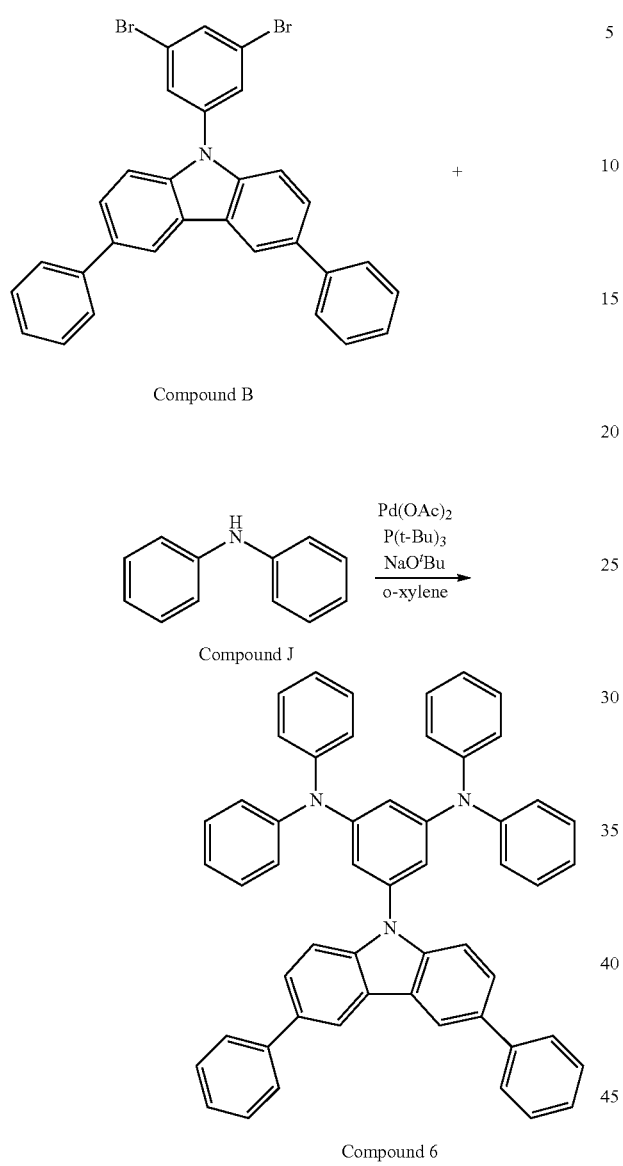

An 150 mL 3-neck round bottom flask was charged with nitrogen, and then a compound B which is 9-(3,5-dibromophenyl)-3,6-diphenyl-9H-carbazole (27.1 mmol, 15.0 g), a compound J which is diphenylamine (59.6 mmol, 10.1 g), palladium acetate (Pd(OAc)$_2$; 2.7 mmol, 0.6 g), sodium tert-butoxide (59.6 mmol, 5.7 g), 70 mL of o-xylene, and tri-tert-butylphosphine (5.4 mmol, 1.3 mL) were added thereto, and the resulting mixture was heated at 130° C. for 4 hours. The solution of the mixture was cooled to room temperature, stirred in 800 mL of methanol for 40 minutes, and filtered, thereby obtaining 20.0 g of a white solid, Compound 6 (yield: 99%).

MALDI-TOF: m/z=729.4469 (C$_{54}$H$_{39}$N$_3$=729.91)

1H-NMR (DMSO, 500 MHz) δ: 8.64 (s, 2H), 7.8 (d, J=7.5 Hz, 4H), 7.73 (d, J=8.5 Hz, 2H), 7.51-7.47 (m, 6H), 7.37-7.32 (m, 10H), 7.20 (d, J=3 Hz, 8H), 7.06 (t, J=7.5 Hz, 4H), 6.68 (s, 1H), 6.60 (s, 2H)

Example 7 (Synthesis of Compound 7)

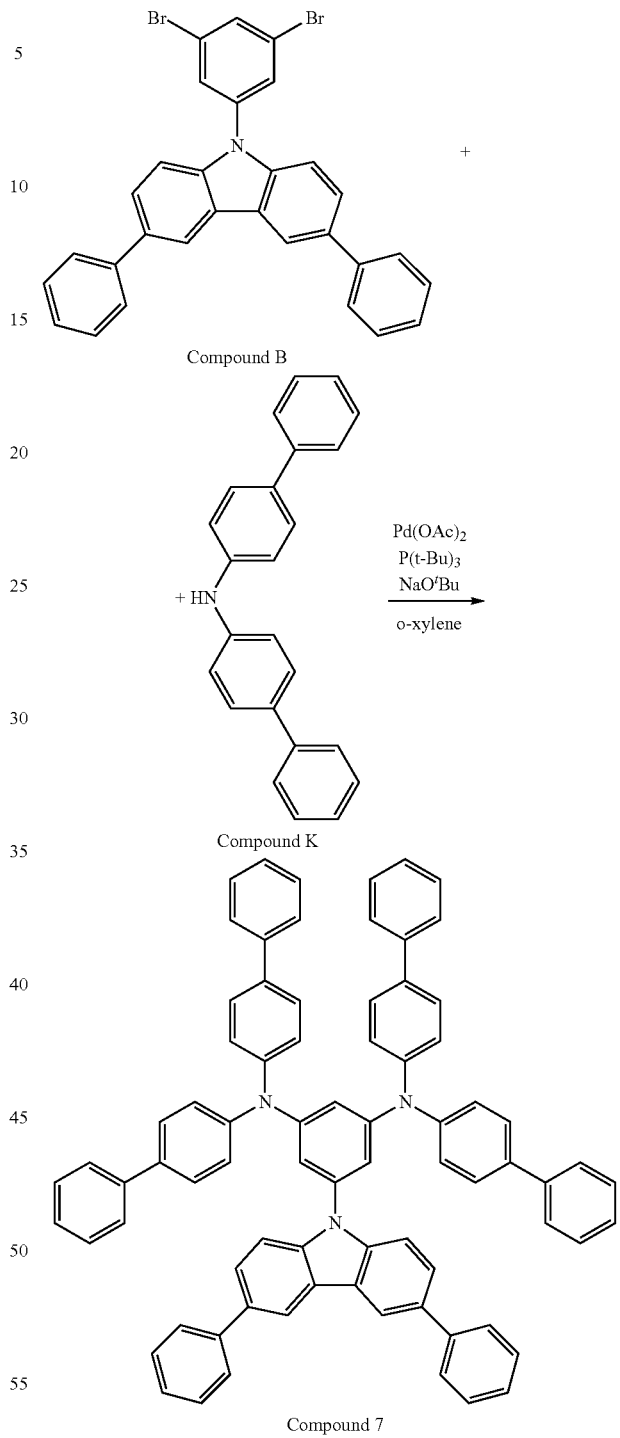

A 500 mL 3-neck round bottom flask was charged with nitrogen, and then a compound B which is 9-(3,5-dibromophenyl)-3,6-diphenyl-9H-carbazole (24.6 mmol, 13.6 g), a compound K which is bis-biphenyl-4-yl-amine (54.1 mmol, 17.4 g), palladium acetate (Pd(OAc)$_2$; 2.5 mmol, 0.6 g), sodium tert-butoxide (54.1 mmol, 5.2 g), 180 mL of o-xylene, and tri-tert-butylphosphine (4.9 mmol, 1.2 mL) were added thereto, and the resulting mixture was heated at 130° C. for 4 hours. The solution of the mixture was cooled to room temperature, and 200 mL of tetrahydrofuran was added thereto. The mixture solution was stirred in 1 L of methanol for 50 minutes, and filtered, thereby obtaining 18.3 g of a white solid, Compound 7 (yield: 74%).

MALDI-TOF: m/z=1033.6634 ($C_{78}H_{55}N_3$=1034.29)

1H-NMR (DMSO, 500 MHz) δ: 8.65 (s, 2H), 7.79-7.76 (m, 6H), 7.69 (d, J=8 Hz, 8H), 7.59 (t, J=7.5 Hz, 10H), 7.48 (t, J=7.5 Hz, 4H), 7.40-7.31 (m, 22H), 6.82-6.80 (m, 3H)

Example 8 (Synthesis of Compound 8)

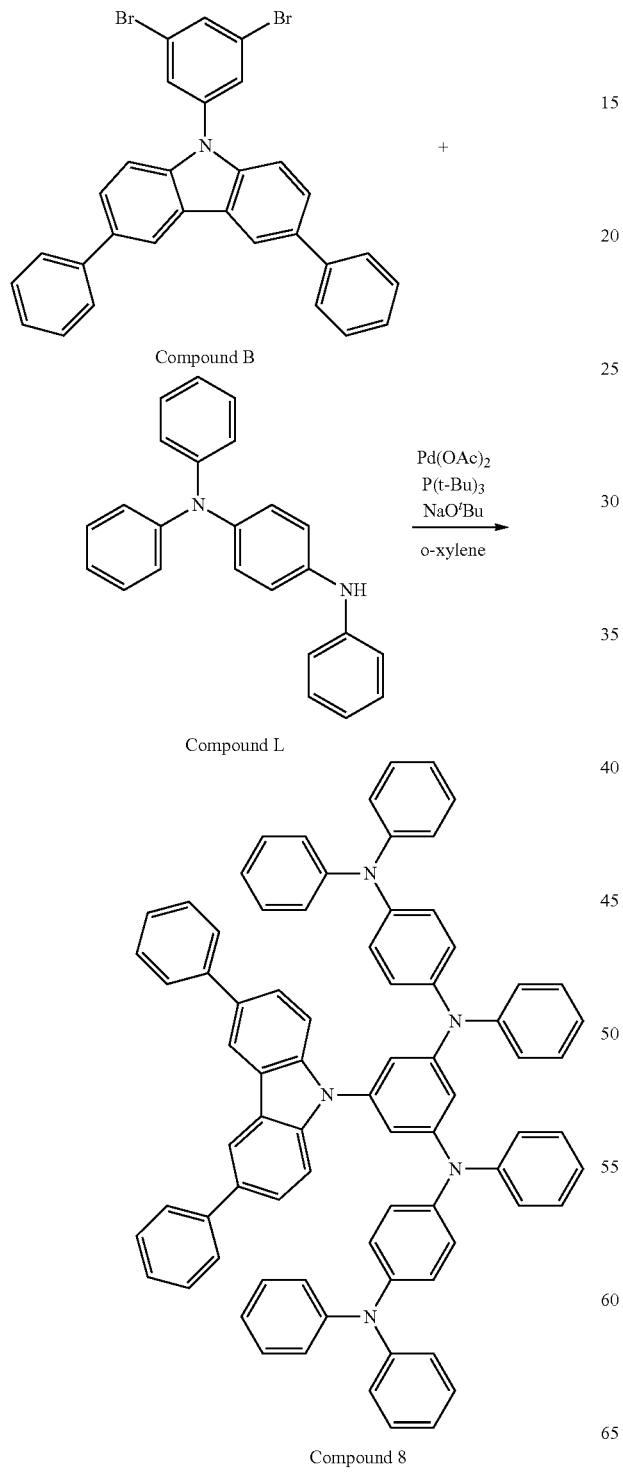

A 250 mL 3-neck round bottom flask was charged with nitrogen, and then a compound B which is 9-(3,5-dibromophenyl)-3,6-diphenyl-9H-carbazole (9.1 mmol, 5.0 g), a compound L which is (4-anilinophenyl)diphenylamine (20.0 mmol, 6.7 g), palladium acetate (Pd(OAc)$_2$; 0.9 mmol, 0.2 g), sodium tert-butoxide (20.0 mmol, 1.9 g), 100 mL of o-xylene, and tri-tert-butylphosphine (1.8 mmol, 0.4 mL) were added thereto, and the resulting mixture was heated at 130° C. for 4 hours. The solution of the mixture was cooled to room temperature, and 100 mL of tetrahydrofuran was added thereto. The mixture solution was stirred in 800 mL of methanol for 25 minutes, and filtered, thereby obtaining 10.0 g of a white solid, Compound 8 (yield: 103%).

MALDI-TOF: m/z=1063.6152 ($C_{78}H_{57}N_5$=1064.32)

1H-NMR (DMSO, 500 MHz) δ: 8.68 (s, 2H), 7.9 (d, J=7.5 Hz, 4H), 7.70 (d, J=8 Hz, 2H), 7.51 (t, J=8 Hz, 6H), 7.38-7.34 (m, 6H), 7.22 (t, J=7 Hz, 12H), 7.17 (d, J=8 Hz, 4H), 7.06 (t, J=6 Hz, 2H), 6.99-6.95 (m, 16H), 6.64 (s, 1H), 6.58 (s, 2H)

Example 9 (Synthesis of Compound 9)

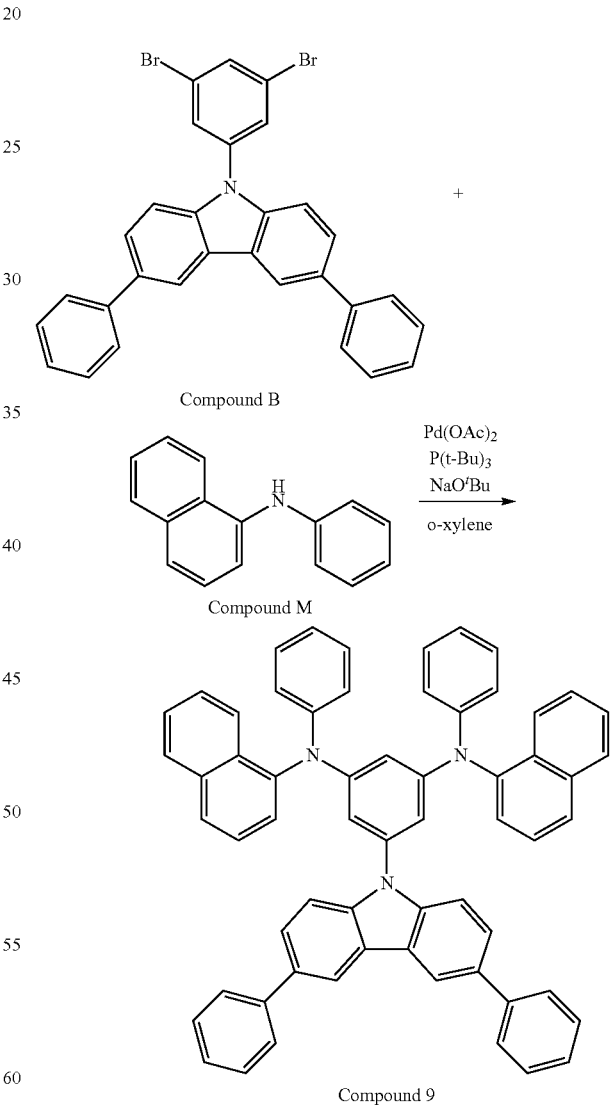

A 150 mL 3-neck round bottom flask was charged with nitrogen, and then a compound B which is 9-(3,5-dibromophenyl)-3,6-diphenyl-9H-carbazole (27.1 mmol, 15.0 g), a compound M which is N-phenyl-1-naphthylamine (59.6 mmol, 13.1 g), palladium acetate (Pd(OAc)$_2$; 2.7 mmol, 0.6 g), sodium tert-butoxide (59.6 mmol, 5.7 g), 70 mL of o-xylene, and tri-tert-butylphosphine (5.4 mmol, 1.3 mL) were added thereto, and the resulting mixture was heated at 130° C. for 4 hours. The solution of the mixture was cooled to room temperature, stirred in 700 mL of methanol for 20 minutes, and filtered, thereby obtaining 20.4 g of a solid, Compound 9 (yield: 91%).

MALDI-TOF: m/z=829.5441 ($C_{62}H_{43}N_3$=830.02) 1H-NMR (DMSO, 500 MHz) δ: 8.55 (s, 2H), 8.03-7.99 (m, 4H), 7.85 (d, J=8 Hz, 2H), 7.71 (d, J=8 Hz, 4H), 7.63-7.59 (m, 4H) 7.54-7.43 (m, 10H), 7.34 (t, J=7.5 Hz, 2H), 7.19 (t, J=8 Hz, 4H), 7.13 (d, J=8 Hz, 4H), 7.02 (s, 2H), 6.95 (t, J=7.5 Hz, 2H), 6.66 (s, 1H), 6.28 (s, 2H)

Example 10 (Synthesis of Compound 10)

A 250 mL 3-neck round bottom flask was charged with nitrogen, and then a compound B which is 9-(3,5-dibromophenyl)-3,6-diphenyl-9H-carbazole (16.6 mmol, 9.2 g), a compound N which is 9H-phenylcarbazole-3-phenylamine (36.6 mmol, 12.2 g), palladium acetate (Pd(OAc)$_2$; 1.7 mmol, 0.4 g), sodium tert-butoxide (36.6 mmol, 3.5 g), 120 mL of o-xylene, and tri-tert-butylphosphine (3.3 mmol, 0.8 mL) were added thereto, and the resulting mixture was heated at 130° C. for 4 hours. The solution of the mixture was cooled to room temperature, and 100 mL of tetrahydrofuran was added thereto. The mixture of the solution was stirred in 800 mL of methanol for 20 minutes, and filtered, thereby obtaining 9.6 g of a white solid, Compound 10 (yield: 99%).

MALDI-TOF: m/z=1059.6636 ($C_{78}H_{53}N_5$=1060.29)

1H-NMR (DMSO, 500 MHz) δ: 8.57 (s, 2H), 8.35 (d, J=7.5 Hz, 2H), 8.31 (s, 2H), 7.65~7.61 (m, 8H), 7.57~7.52 (m, 10H), 7.46 (m, 6H), 7.35~7.27 (m, 18H), 6.96 (s, 2H), 6.78 (s, 1H), 6.53 (s, 2H)

Example 11 (Synthesis of Compound 11)

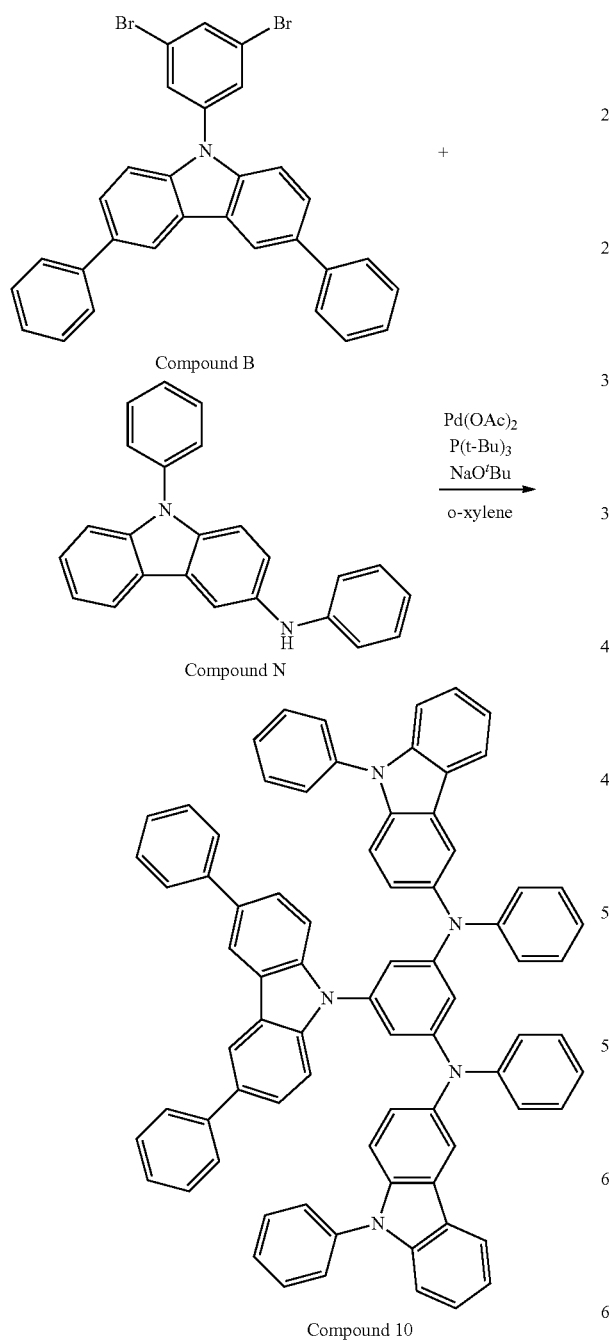

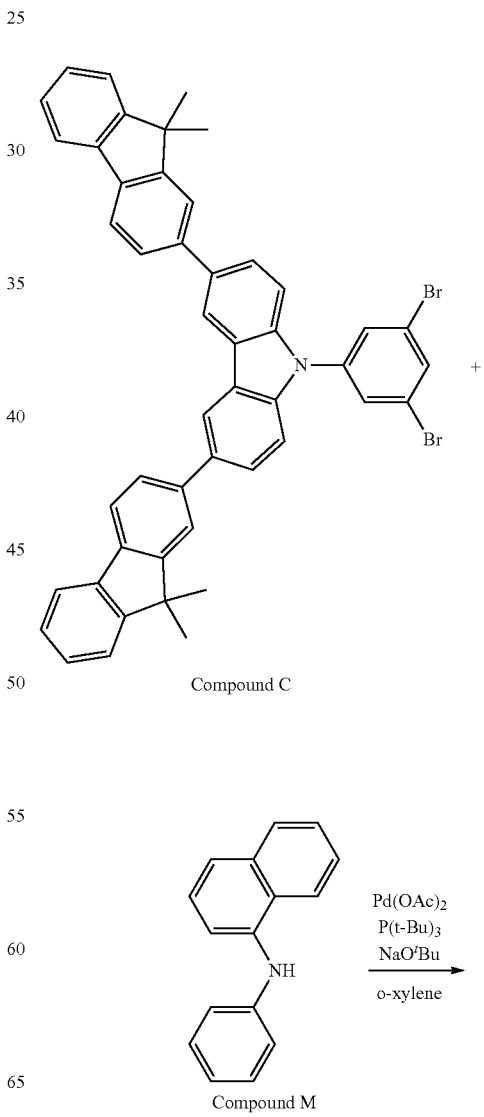

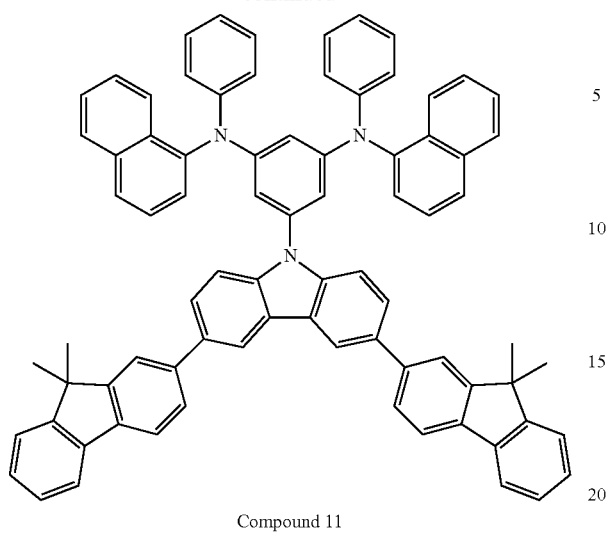

Compound 11

An 100 mL 3-neck round bottom flask was charged with nitrogen, and then a compound C which is 9-(3,5-dibromophenyl)-3,6-bis(9,9-dimethyl-9H-fluoren-2-yl)-9H-carbazole (13.4 mmol, 10.5 g), a compound M which is N-phenyl-1-naphthylamine (29.4 mmol, 5.0 g), palladium acetate (Pd(OAc)$_2$; 1.3 mmol, 0.3 g), sodium tert-butoxide (29.4 mmol, 2.8 g), 60 mL of o-xylene, and tri-tert-butylphosphine (2.7 mmol, 0.6 mL) were added thereto, and the resulting mixture was heated at 130° C. for 5 hours. The solution of the mixture was cooled to room temperature, stirred in 240 mL of methanol for 30 minutes, and filtered, thereby obtaining 12.1 g of a solid, Compound 11 (yield: 85%).

MALDI-TOF: m/z=1061.7176 ($C_{80}H_{59}N_3$=1062.34)

Example 12 (Synthesis of Compound 12)

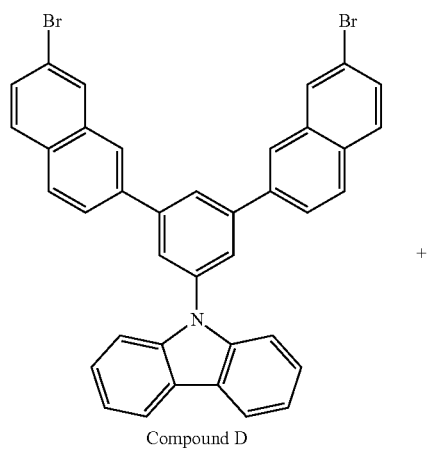

Compound D

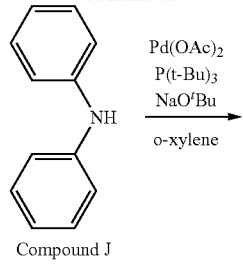

Compound J

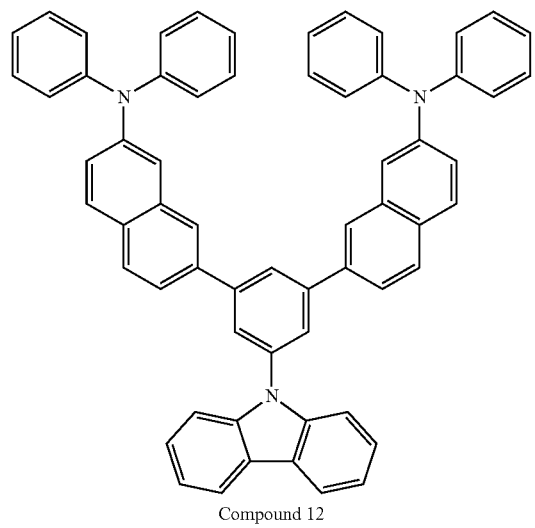

Compound 12

A 100 mL 3-neck round bottom flask was charged with nitrogen, and then a compound D which is 9-(3,5-bis(7-bromonaphthalene-2-yl)phenyl)-9H-carbazole (11.9 mmol, 7.8 g), a compound J which is diphenylamine (26.3 mmol, 4.4 g), palladium acetate (Pd(OAc)$_2$; 1.2 mmol, 0.3 g), sodium tert-butoxide (26.3 mmol, 2.5 g), 70 mL of o-xylene, and tri-tert-butylphosphine (2.4 mmol, 0.6 mL) were added thereto, and the resulting mixture was heated at 130° C. for 4 hours. The solution of the mixture was cooled to room temperature, stirred in 500 mL of methanol for 25 minutes, and filtered, thereby obtaining 7.8 g of a solid, Compound 12 (yield: 80%).

MALDI-TOF: m/z=829.2741 ($C_{62}H_{43}N_3$=830.02)

Example 13 (Synthesis of Compound 13)

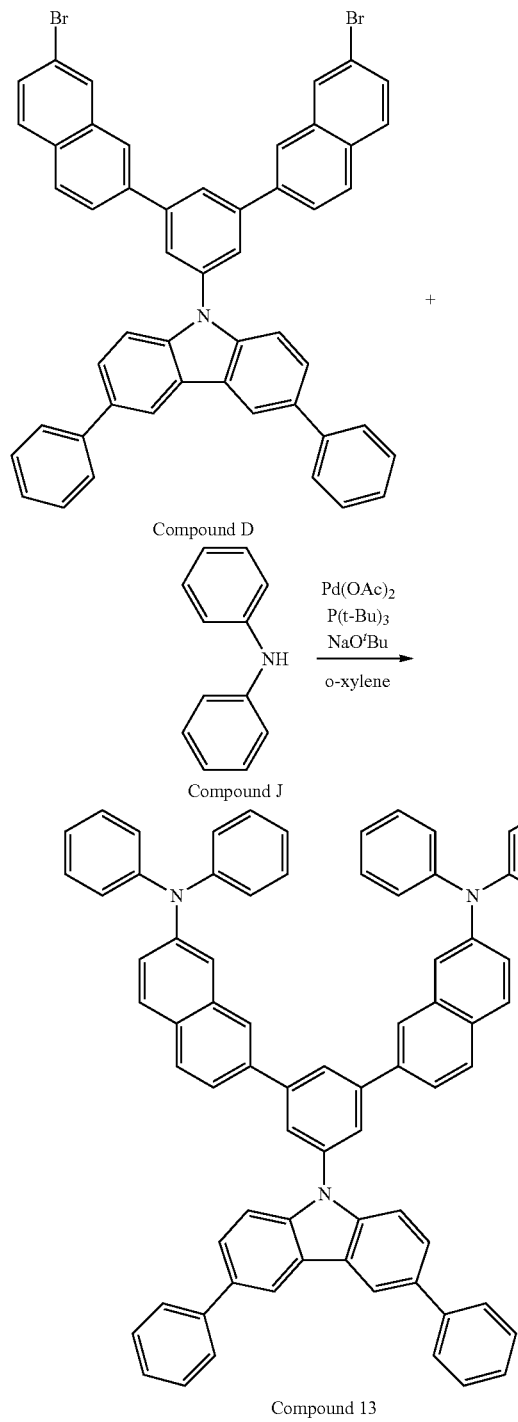

Compound 13

Example 14 (Synthesis of Compound 14)

130° C. for 4 hours. The solution of the mixture was cooled to room temperature, stirred in 240 mL of methanol for 25 minutes, and filtered, thereby obtaining 6.9 g of a solid, Compound 13 (yield: 78%).

MALDI-TOF: m/z=981.8502 ($C_{74}H_{51}N_3$=982.22)

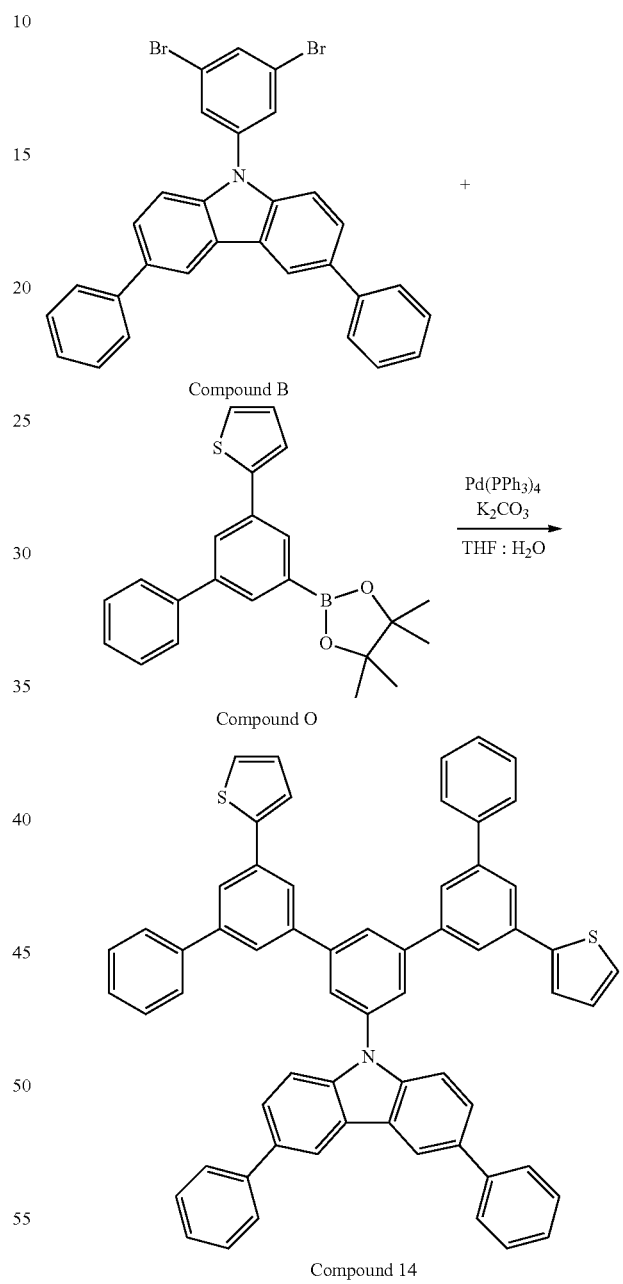

Compound 14

An 100 mL 3-neck round bottom flask was charged with nitrogen, and then a compound D which is 9-(3,5-bis(7-bromonaphthalene-2-yl)phenyl)-3,6-diphenyl-9H-carbazole (9.1 mmol, 7.3 g), a compound J which is diphenylamine (20.0 mmol, 3.4 g), palladium acetate (Pd(OAc)$_2$; 0.9 mmol, 0.2 g), sodium tert-butoxide (19.9 mmol, 1.9 g), 60 mL of o-xylene, and tri-tert-butylphosphine (1.8 mmol, 0.4 mL) were added thereto, and the resulting mixture was heated at A 250 mL 3-neck round bottom flask was charged with nitrogen, and then a compound B which is 9-(3,5-dibromophenyl)-3,6-diphenyl-9H-carbazole (19.9 mmol, 11.0 g), a compound O which is 4,4,5,5-tetramethyl-2-(5-(thiophen-2-yl)biphenyl-3-yl)-1,3,2-dioxaborolane (43.7 mmol, 15.8 g), tetrakis(triphenylphosphine)palladium (Pd(PPh$_3$)$_4$; 1.59 mmol, 1.8 g), potassium carbonate (43.7 mmol, 6.0 g), 65 mL of tetrahydrofuran, and 25 mL of distilled water were added thereto, and heated at 130° C. for 3 hours. The resulting mixture was cooled to room temperature, and 30 mL of distilled water was added thereto, thereby separating an organic layer and an aqueous solution layer. The organic layer was put into 300 mL of methanol, stirred for 30 minutes, and filtered, thereby obtaining 12.4 g of a solid, Compound 14 (yield: 72%).

MALDI-TOF: m/z=863.4301 ($C_{62}H_{41}NS_2$=864.13)

Example 15 (Synthesis of Compound 15)

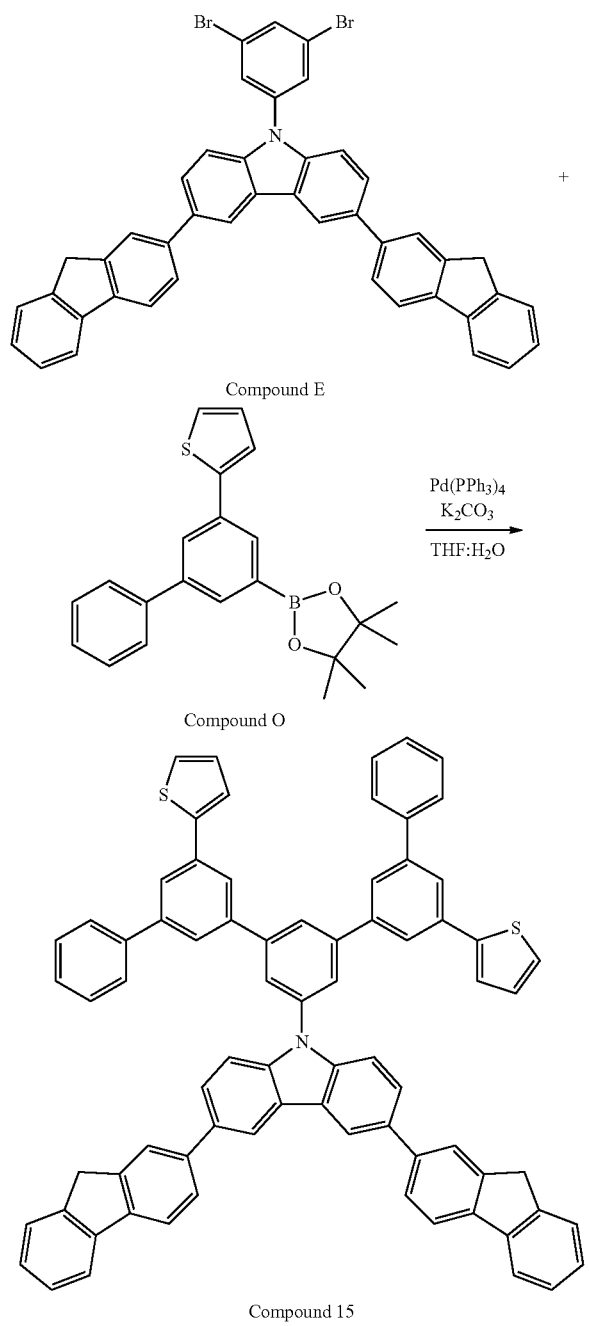

Compound E

Compound O

Compound 15

A 250 mL 3-neck round bottom flask was charged with nitrogen, and then a compound E which is 9-(3,5-dibromophenyl)-3,6-di(9H-fluoren-2-yl)-9H-carbazole (12.2 mmol, 8.9 g), a compound O which is 4,4,5,5-tetramethyl-2-(5-(thiophen-2-yl)biphenyl-3-yl)-1,3,2-dioxaborolane (26.8 mmol, 9.7 g), tetrakis(triphenylphosphine)palladium (Pd(PPh$_3$)$_4$; 1.0 mmol, 1.1 g), potassium carbonate (26.8 mmol, 3.7 g), 65 mL of tetrahydrofuran, and 35 mL of distilled water were added thereto, and heated at 130° C. for 5 hours. The resulting solution was cooled to room temperature, and 30 mL of distilled water was added to separate an organic layer and an aqueous solution layer. The organic layer was put into 700 mL of methanol, stirred for 60 minutes, and filtered, thereby obtaining 9.7 g of a solid, Compound 15 (yield: 76%).

MALDI-TOF: m/z=1039.9746 ($C_{76}H_{49}NS_2$=1040.34)

Example 16 (Synthesis of Compound 16)

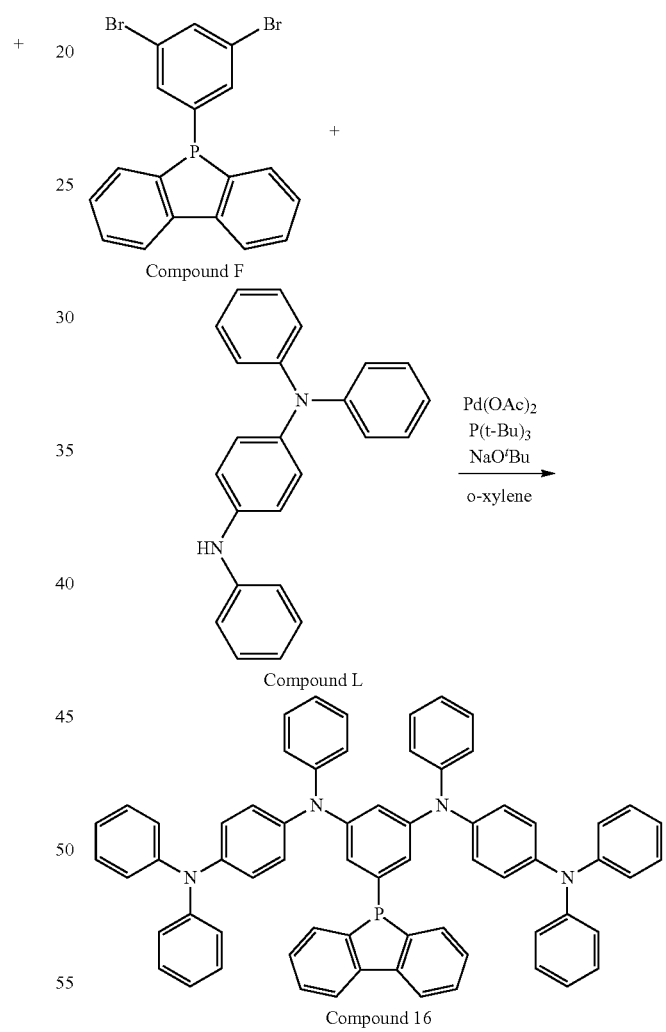

Compound F

Compound L

Compound 16

An 100 mL 3-neck round bottom flask was charged with nitrogen, and then a compound F which is 5-(3,5-dibromophenyl)-5H-pentaphenylphosphole (24.6 mmol, 10.3 g), a compound L which is (4-anilinophenyl)diphenylamine (54.1 mmol, 18.2 g), palladium acetate (Pd(OAc)$_2$) (2.5 mmol, 0.6 g), sodium tert-butoxide (54.1 mmol, 5.2 g), 65 mL of o-xylene, and tri-tert-butylphosphine (4.9 mmol, 1.2 mL) were added thereto, and heated at 130° C. for 5 hours. The resulting solution was cooled to room temperature, stirred in 325 mL of methanol for 40 minutes, and filtered, thereby obtaining 14.2 g of a white solid, Compound 16 (yield: 62%).

MALDI-TOF: m/z=927.3232 ($C_{66}H_{49}N_4P$=928.37)

Example 17 (Synthesis of Compound 17)

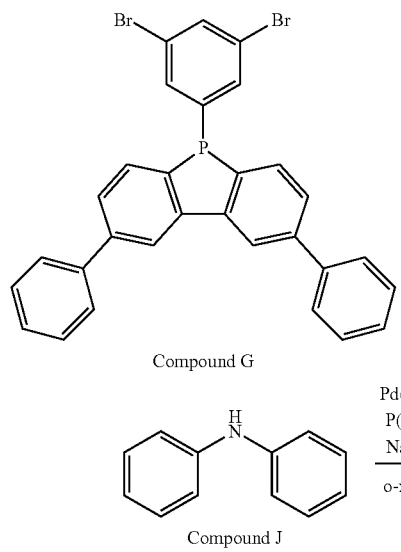

Example 18 (Synthesis of Compound 18)

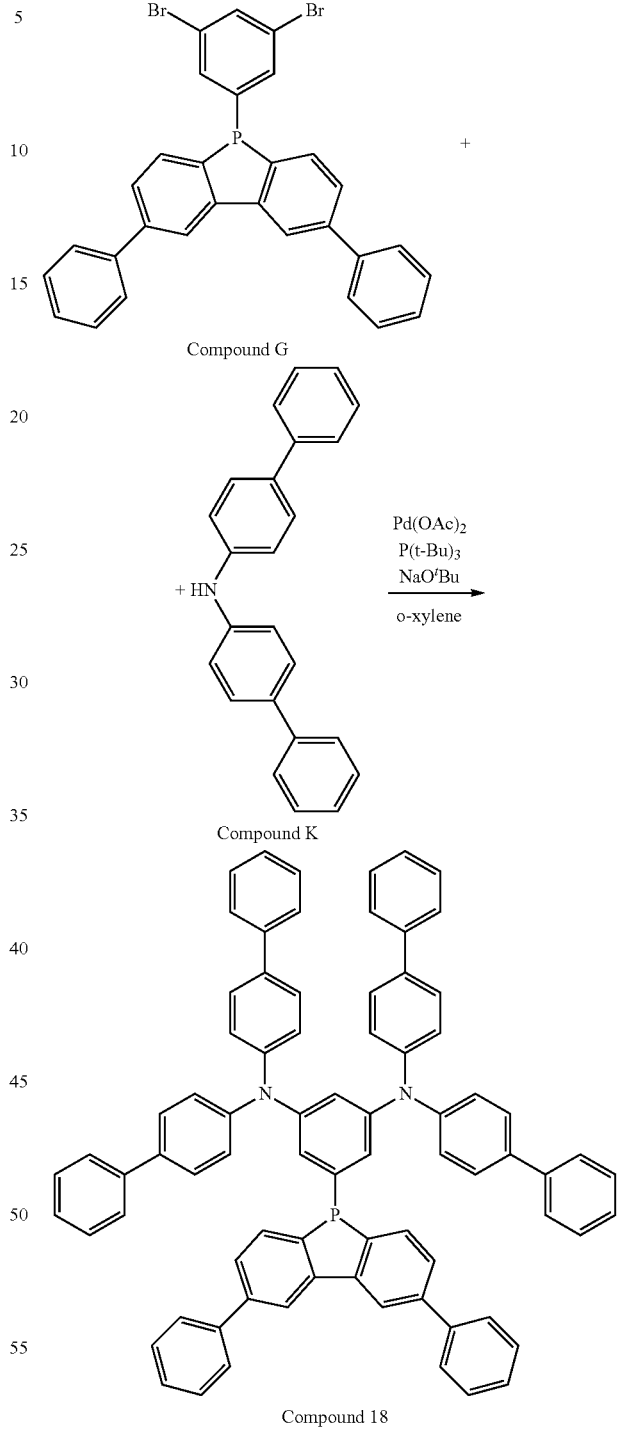

An 1000 mL 3-neck round bottom flask was charged with nitrogen, and then a compound G which is 5-(3,5-dibromophenyl)-3,6-diphenyl-5H-pentaphenylphosphole (19.3 mmol, 11.0 g), a compound J which is diphenylamine (42.5 mmol, 7.19 g), palladium acetate (Pd(OAc)$_2$) (1.93 mmol, 0.4 g), sodium tert-butoxide (42.5 mmol, 4.1 g), 70 mL of o-xylene and tri-tert-butylphosphine (3.86 mmol, 0.9 mL) were added thereto, and heated at 130° C. for 7 hours. The resulting solution was cooled to room temperature, stirred in 400 ml of methanol for 40 minutes, and filtered, thereby obtaining 12.0 g of a white solid, Compound 17 (yield: 83%).

MALDI-TOF: m/z=745.92 ($C_{54}H_{39}N_2P$=746.29)

A 250 mL 3-neck round bottom flask was charged with nitrogen, and then a compound G which is 5-(3,5-dibromophenyl)-3,6-diphenyl-5H-pentaphenylphosphole (21.0 mmol, 12.0 g), a compound K which is bis-biphenyl-4-yl-amine (46.2 mmol, 14.8 g), palladium acetate (Pd(OAc)$_2$) (2.1 mmol, 0.5 g), sodium tert-butoxide (46.2 mmol, 4.4 g), 70 mL of o-xylene, and tri-tert-butylphosphine (4.2 mmol, 1 mL) were added thereto, and heated at 130° C. for 5 hours.

The resulting solution was cooled to room temperature, and 30 mL of tetrahydrofuran was added thereto. The solution of the mixture was stirred in 500 mL of methanol for 30 minutes, and filtered, thereby obtaining 13.4 g of a white solid, Compound 18 (yield: 61%).

MALDI-TOF: m/z=1050.96 ($C_{78}H_{55}N_2P$=1051.40)

Example 19 (Synthesis of Compound 19)

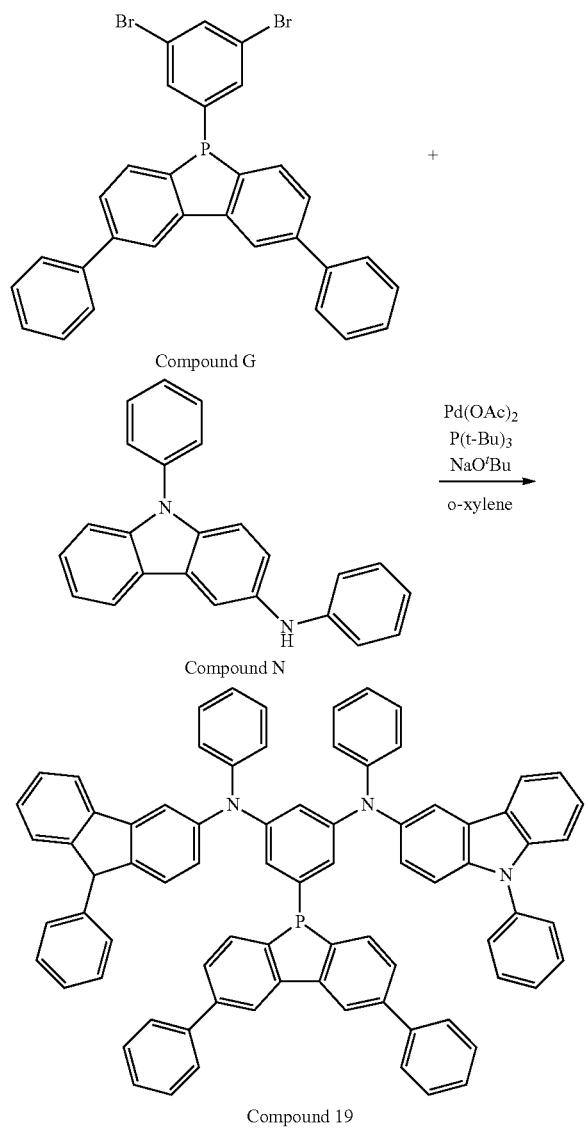

Example 20 (Synthesis of Compound 20)

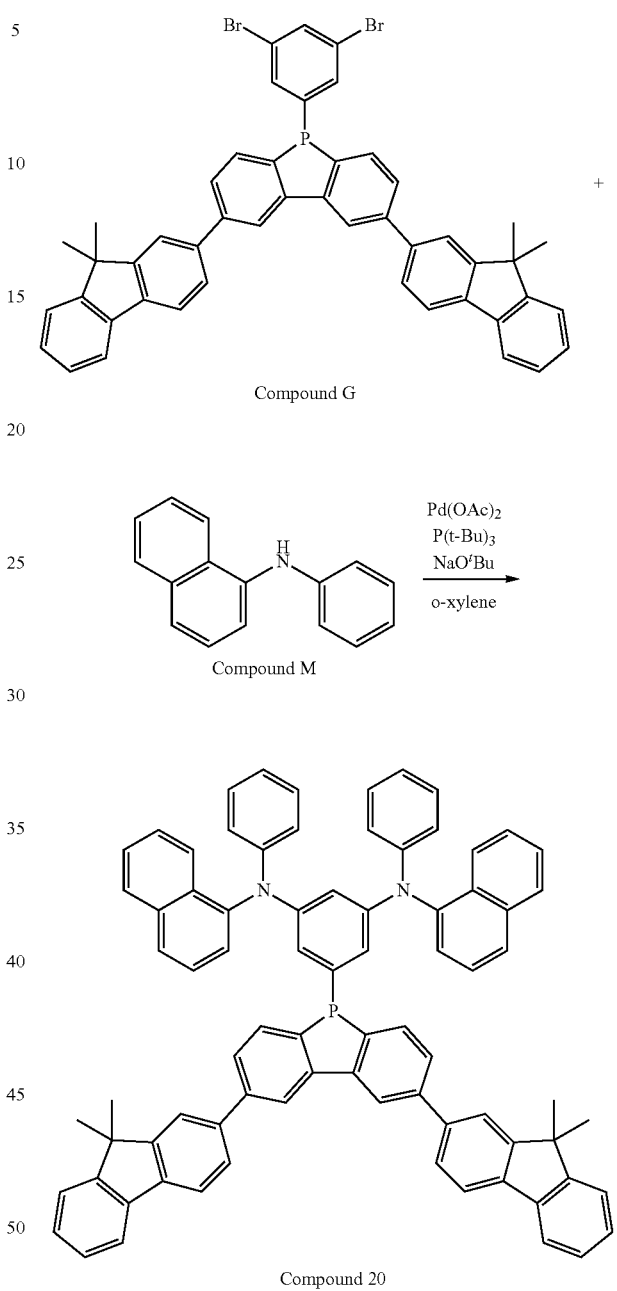

A 250 mL 3-neck round bottom flask was charged with nitrogen, and then a compound G which is 5-(3,5-dibromophenyl)-3,6-diphenyl-5H-pentaphenylphosphole (18.4 mmol, 10.5 g), a compound N which is 9H-phenylcarbazole-3-phenylamine (40.5 mmol, 13.5 g), palladium acetate (Pd(OAc)$_2$) (1.8 mmol, 0.4 g), sodium tert-butoxide (40.5 mmol, 3.9 g), 70 mL of o-xylene, and tri-tert-butylphosphine (3.7 mmol, 0.9 mL) were added thereto, and heated at 130° C. for 6 hours. The resulting solution was cooled to room temperature, and 30 mL of tetrahydrofuran was added thereto. The solution of the mixture was stirred in 500 mL of methanol for 60 minutes, and filtered, thereby obtaining 12.8 g of a white solid, Compound 19 (yield: 64%)

MALDI-TOF: m/z=1075.87 ($C_{78}H_{53}N_4P$=1076.40).

An 100 mL 3-neck round bottom flask was charged with nitrogen, and then a compound H which is 5-(3,5-dibromophenyl)-3,6-bis(9,9-dimethyl-9H-fluoren-2-yl)-5H-pentaphenylphosphole (7.5 mmol, 10.5 g), a compound M which is N-phenyl-1-naphthylamine (19.7 mmol, 4.3 g), palladium acetate (Pd(OAc)$_2$) (0.9 mmol, 0.2 g), sodium tert-butoxide (19.7 mmol, 1.9 g), 60 mL of o-xylene, and tri-tert-butylphosphine (1.8 mmol, 0.4 mL) were added thereto, and heated at 130° C. for 6 hours. The resulting solution was cooled to room temperature, stirred in 240 mL of methanol for 25 minutes, and filtered, thereby obtaining 7.2 g of a solid, Compound 20 (yield: 74%).

MALDI-TOF: m/z=1077.9233 ($C_{80}H_{59}N_2P$=1078.44)

Example 21 (Synthesis of Compound 21)

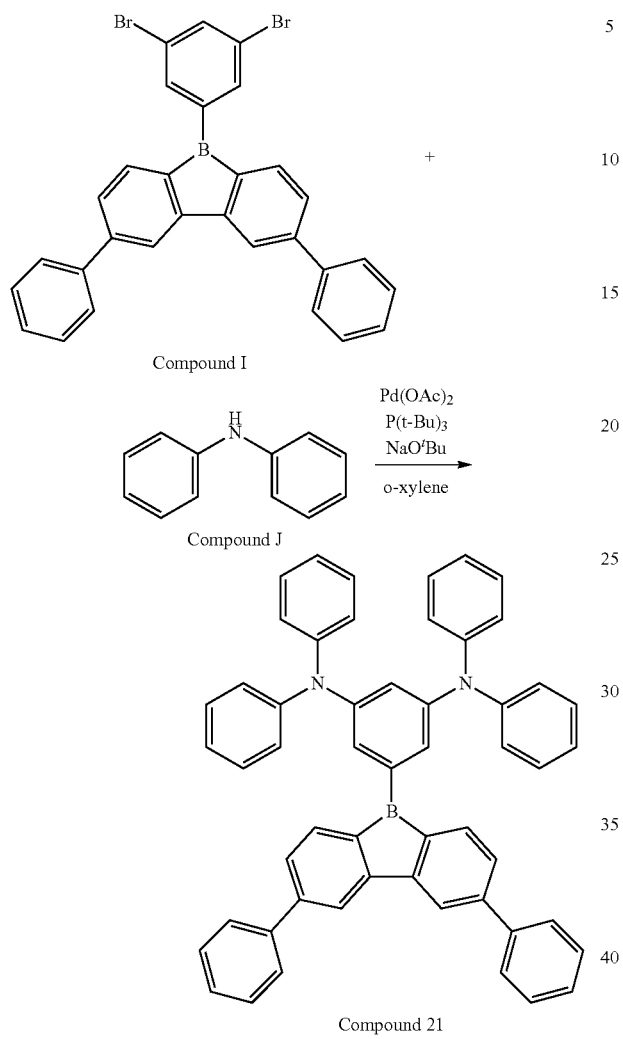

Compound 21

An 100 mL 3-neck round bottom flask was charged with nitrogen, and then a compound I which is 5-(3,5-dibomophenyl)-2.8-diphenyl-5H-dibenzoborole (18.2 mmol, 10.0 g), a compound J which is diphenylamine (40.0 mmol, 6.8 g), palladium acetate (Pd(OAc)$_2$) (1.8 mmol, 0.4 g), sodium tert-butoxide (6.8 mmol, 0.6 g), 50 mL of o-xylene, and tri-tert-butylphosphine (3.6 mmol, 0.8 mL) were added thereto, and heated at 130° C. for 4 hours. The resulting solution was cooled to room temperature, stirred in 200 mL of methanol for 20 minutes, and filtered, thereby obtaining 12.7 g of a solid, Compound 21 (yield: 96%).

MALDI-TOF: m/z=725.9258 (C$_{54}$H$_{39}$BN$_2$=726.32)

Purification was performed with respect to the synthesized compounds of Examples 1 to 21 to increase purity. Since the purity of an organic material contained in an OED was a factor having an influence on an emitting characteristic of the device, when impurities were mixed with an organic material, the device could have extinction or degradation of efficiency. To prevent this, purification was usually performed. As a result of the high degree of purification using recrystallization and sublimation to remove impurities contained in the compounds of Examples 1 to 21, organic materials having a high purity of 99.95% or more were obtained.

Comparative Example 1

N,N'-diphenyl-N,N'-bis(1-naphthyl)-1,1'-biphenyl-4,4'-diamine (NPB) conventionally used as a hole transport material was used as Comparative Example 1.

Comparative Example 2

A material of the following Formula was synthesized to be used in Comparative Example 2.

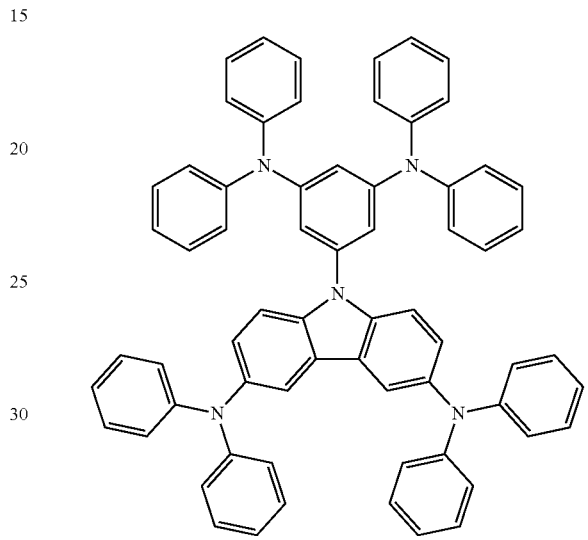

Comparative Example 3

A material of the following Formula was synthesized to be used in Comparative Example 3.

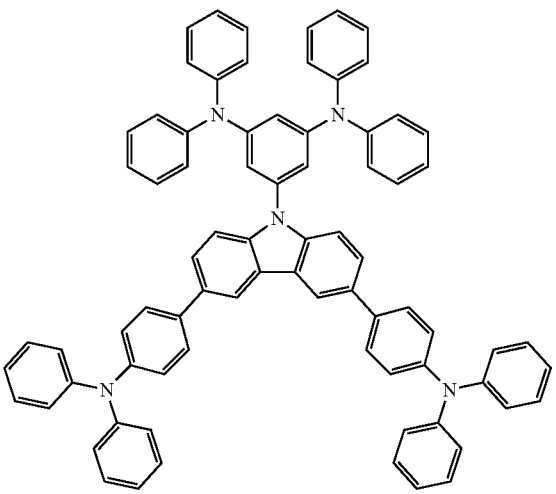 [SMILES: c1ccc(N(c2ccccc2)c2ccc(-c3ccc4c(c3)c3cc(-c5ccc(N(c6ccccc6)c6ccccc6)cc5)ccc3n4-c3cc(N(c4ccccc4)c4ccccc4)cc(N(c4ccccc4)c4ccccc4)c3)cc2)cc1]

Comparative Example 4

A material of the following Formula was synthesized to be used in Comparative Example 4.

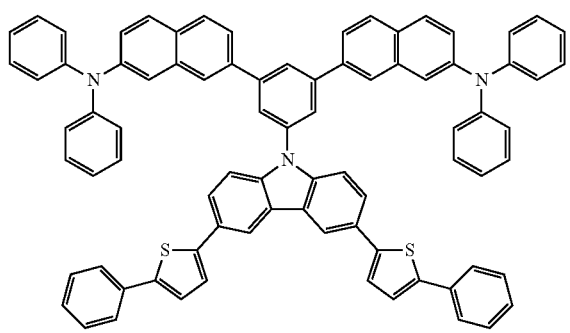 [SMILES: c1ccc(-c2ccc(-c3ccc4c(c3)c3cc(-c5ccc(-c6ccccc6)s5)ccc3n4-c3cc(-c4ccc5ccc(N(c6ccccc6)c6ccccc6)cc5c4)cc(-c4ccc5ccc(N(c6ccccc6)c6ccccc6)cc5c4)c3)s2)cc1]

Experimental Example 1: Measurement of Maximum Absorption Wavelength

The maximum absorption wavelength was measured by dissolving the compounds according to Examples 1 to 10 and the compound according to Comparative Example 1 in tetrahydrofuran (THF) to obtain a concentration of $10^{-5}$ M using a UV/Vis spectrophotometer. The results are shown in Tables 1 and 2.

Experimental Example 2: Measurement of Highest Occupied Molecular Orbital (HOMO) Energy Level The HOMO energy levels of the compounds prepared according to Examples 1 to 10 and the compound prepared according to Comparative Example 1 were measured using cyclic voltammetry (CV). Specifically, 0.1 M of a support electrolyte, tetrabutylammonium hexafluorophosphate, was dissolved in 20 mL of a solvent, methylene chloride, 0.5 mM of each of the prepared compositions of example 1 to 10 and the composition of Comparative Example 1 was dissolved, and a current value was measured within a voltage range of −0.1 to 1.0 V. The results are shown in Tables 1 and 2.

Experimental Example 3: Measurement of Lowest Unoccupied Molecular Orbital (LUMO) Energy Level A LUMO value was calculated according to General formula 1 using a bandgap obtained from an edge of a UV absorption wavelength measured in Experimental Example 1. The results are shown in Tables 1 and 2.

|LUMO value|=|HOMO value|−bandgap   [General formula 1]

In General formula 1, the LUMO value and the HOMO value are an absolute value of the LUMO energy level and an absolute value of the HOMO energy level, respectively.

Experimental Example 4: Measurement of Glass Transition Temperature (Tg)

The glass transition temperatures of the compounds according to Examples 1 to 10 and the compound according to Comparative Example 1 were measured using a differential scanning calorimeter (DSC). The temperature was increased by 10° C. per minute, and regulated in a temperature range of −50 to 470° C. The results are shown in Tables 1 and 2.

TABLE 1

| Category | Example 1 | 2 | 3 | 4 | 5 |
|---|---|---|---|---|---|
| UV maximum absorption wavelength (nm) | 294 | 332 | 293 | 293 | 295 |
| HOMO level (eV) | 5.51 | 5.2 | 5.56 | 5.53 | 5.04 |
| LUMO level (eV) | 2.16 | 2.1 | 2.30 | 2.47 | 2.02 |
| Glass transition temperature (° C.) | 117.4 | 131.3 | 104.3 | 148.7 | 148.5 |

TABLE 2

| Category | Example 6 | 7 | 8 | 9 | 10 | Comparative Example 1 |
|---|---|---|---|---|---|---|
| UV maximum absorption wavelength (nm) | 300 | 332 | 305 | 299 | 304 | 342 |
| HOMO level (eV) | 5.29 | 5.20 | 4.88 | 5.34 | 5.02 | 5.39 |
| LUMO level (eV) | 1.94 | 2.10 | 1.62 | 2.04 | 1.92 | 2.27 |
| Glass transition temperature (° C.) | 119.3 | 131.3 | 135.7 | 129.8 | 165.6 | 96 |

Referring to Tables 1 and 2, it can be noted that the compounds based on Examples 1 to 10 had a HOMO value of 5.6 eV or less, a LUMO value of 2.5 eV or less, and a glass transition temperature of 100° C. or more. Particularly, it is confirmed that the glass transition temperature of the compound based on Example 10 was 165.6° C., which was approximately 69° C. or more higher than that of the compound based on Comparative Example 1, and thus it can be noted that the compound prepared in the present invention could enhance the thermal stability and efficiency of the device.

Experimental Example 5: Evaluation of Physical Properties of Device

1. Manufacturing of OED

A hole transport material, which is the compound based on Example 1, and a p-type dopant material, which is HAT-CN having the structure of Formula 9, were deposited together on an ITO electrode. Specifically, the compound based on Example 1 as a hole transport material (host) was deposited on the ITO electrode at a rate of approximately 1 Å/sec, and the p-type dopant having the structure of Formula 9 was co-deposited thereon at a rate of 0.05 Å/sec, thereby forming a first hole transport layer having a thickness of approximately 1,250 Å. The compound based on Example 1 was deposited on the first hole transport layer to have a thickness of approximately 340 Å, thereby forming a second hole transport layer. Subsequently, an emitting layer formed by doping tris(8-hydroxyquinoline)aluminum (Alq3) having a structure of Formula 10 with 2 parts by weight of C545T having a structure of Formula 11 was formed on the second hole transport layer to have a thickness of approximately 340 Å. An electron transport layer in which BPhen having a structure of Formula 12 was mixed with Liq having a structure of Formula 13 in a weight ratio of approximately 50:50 was formed on the formed emitting layer to have a thickness of approximately 325 Å, and Liq having a structure of Formula 13 was formed on the electron transport layer to have a thickness of approximately 10 Å. Afterward, an aluminum electrode was stacked to have a thickness of approximately 1000 Å, thereby manufacturing an OED 1.

[Formula 9]

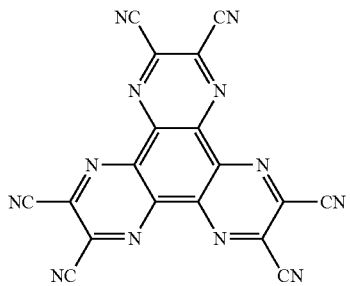

[Formula 10]

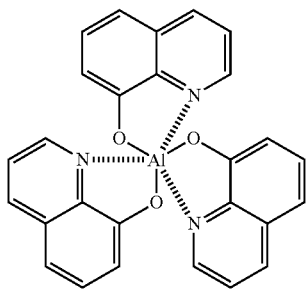

[Formula 11]

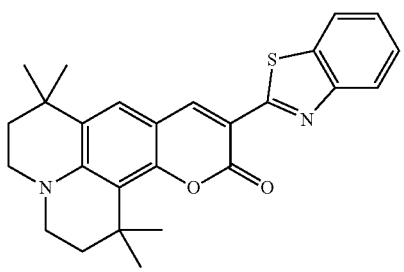

[Formula 12]

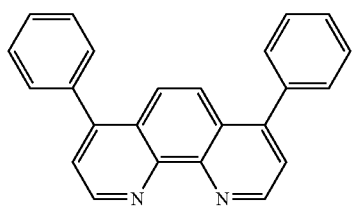

[Formula 13]

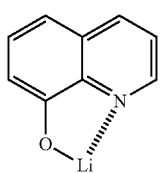

OEDs 2 to 21 respectively including the compounds of Examples 2 to 21 were manufactured by substantially the same method as used in the manufacturing of the OED 1.

In addition, Comparative devices 1 to 3 respectively including the compounds of Comparative Examples 2 to 4 were manufactured by substantially the same method used in the manufacture of the OED 1.

2. Measurement of Power Efficiency

The power efficiency of the OEDs 1 to 21 manufactured as described above and Comparative devices 1 to 3 were measured. The power efficiency was measured based on a value when a luminescence was 500 cd/m$^2$, the measurement results are shown in Table 3, and the unit is 1 m/W.

3. Measurement of Lifetime of Device

The measurement of the lifetime was performed with respect to OEDs 1 to 21 based on the present invention and Comparative devices 1 to 3 through the following process. Each of the manufactured OEDs and the comparative devices were cured by dispensing a UV-curable sealant on an edge of a cover glass, sealing the OED with the cover glass, and radiating UV rays in a glove box under/in a nitrogen atmosphere. Afterward, the lifetime of the device was measured in an oven at 85° C. T75 the time when the luminance of the device is 75% of the initial luminance at an initial luminance of the device of 1,000 cd/m2. The measurement results are shown in Table 3, and the unit is hr.

TABLE 3

| Category | Power efficiency [lm/W] | Lifetime T75 at 85° C.[hr] |
| --- | --- | --- |
| OED 1 | 4.13 | 54 |
| OED 2 | 3.82 | 47 |
| OED 3 | 4.58 | 58 |
| OED 4 | 3.95 | 51 |
| OED 5 | 4.75 | 62 |
| OED 6 | 3.77 | 46 |
| OED 7 | 5.42 | 68 |
| OED 8 | 6.23 | 79 |
| OED 9 | 4.95 | 63 |
| OED 10 | 5.33 | 67 |
| OED 11 | 4.92 | 63 |
| OED 12 | 3.98 | 51 |
| OED 13 | 3.57 | 45 |
| OED 14 | 3.63 | 47 |
| OED 15 | 3.81 | 48 |
| OED 16 | 4.23 | 54 |
| OED 17 | 3.61 | 46 |
| OED 18 | 4.87 | 62 |
| OED 19 | 4.75 | 60 |
| OED 20 | 4.53 | 58 |
| OED 21 | 3.51 | 45 |
| Comparative device 1 | 3.46 | 43 |
| Comparative device 2 | 3.48 | 44 |
| Comparative device 3 | 3.34 | 41 |

Referring to Table 3, it can be noted that OEDs 1 to 21 respectively including the compounds of Examples 1 to 21 based the present invention had relatively higher power efficiency than those of the Comparative devices 1 to 3.

In addition, it can be noted that the lifetimes of the OEDs including the compounds of Examples 1 to 21 based on the present invention had a relatively longer lifetime than those of the Comparative devices 1 to 3.

While the invention has been shown and described with reference to certain exemplary embodiments thereof, it will be understood by those skilled in the art that various modifications in form and details may be made therein without departing from the spirit and scope of the invention as defined by the appended claims.

| <Description of Reference Numbers of Drawings> | |
| --- | --- |
| 10: ITO electrode | 20, 21: hole transport layer |
| 22: first hole transport layer | 23: second hole transport layer |
| 30: emitting layer | 40: electron transport layer |
| 50: electron injection layer | 60: aluminum electrode |

What is claimed is:

1. A compound represented by any one of Formulae 1-1 to 1-4, 1-6 to 1-9, 1-11, 1-14 to 1-16, 1-18, 1-19, and 4-1 to 4-4:

1-1
1-2
1-3
1-4
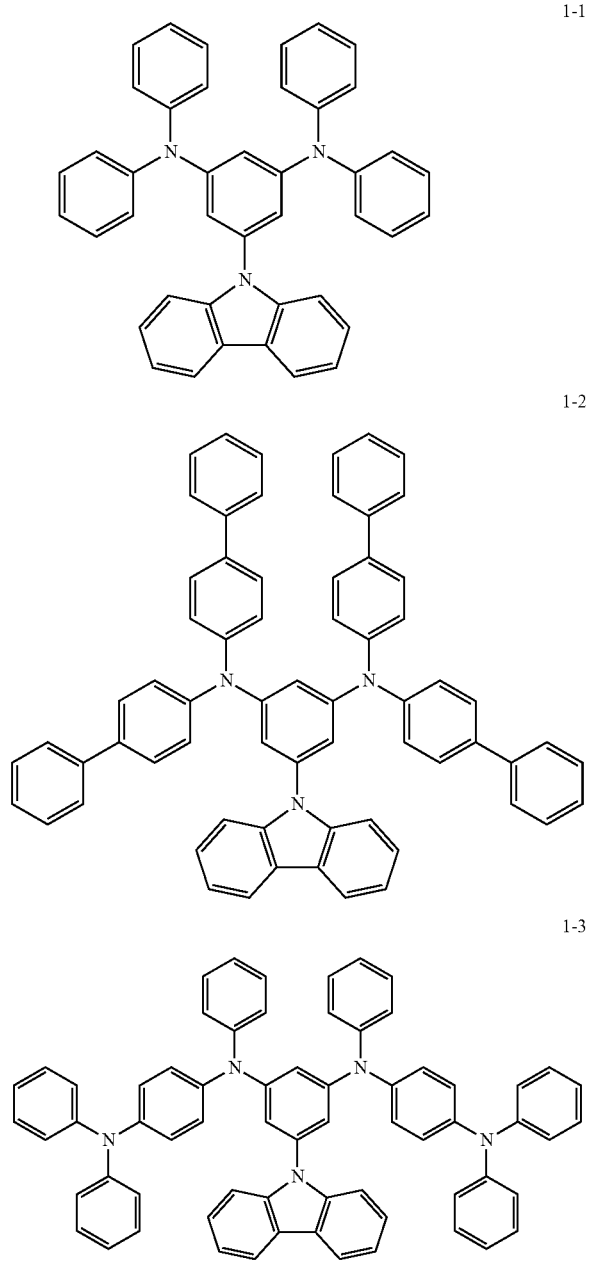
-continued
1-6
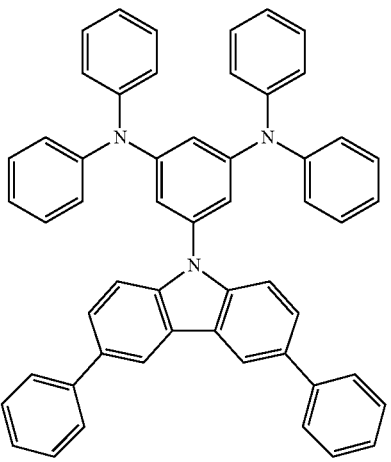
1-7
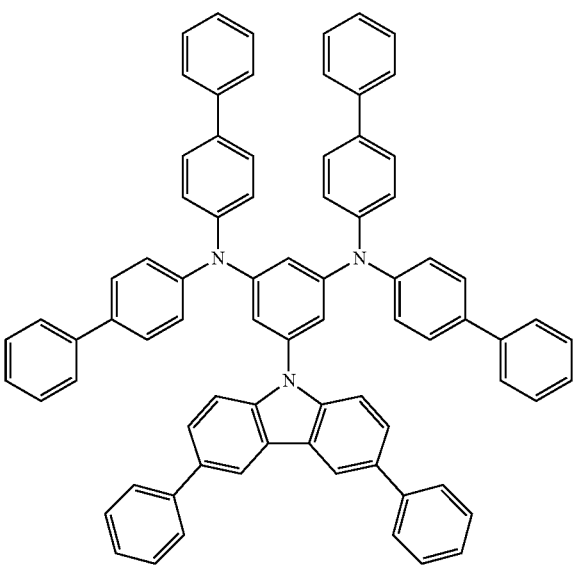
1-8
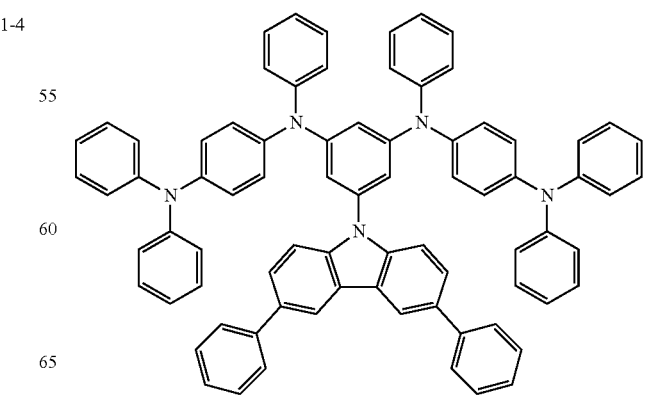
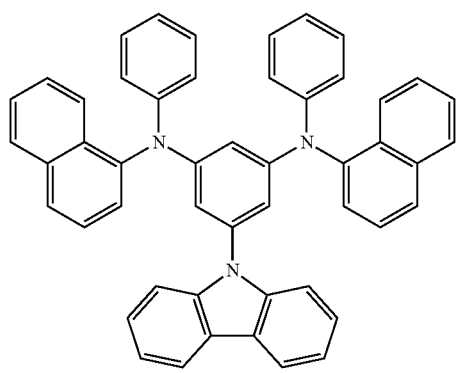

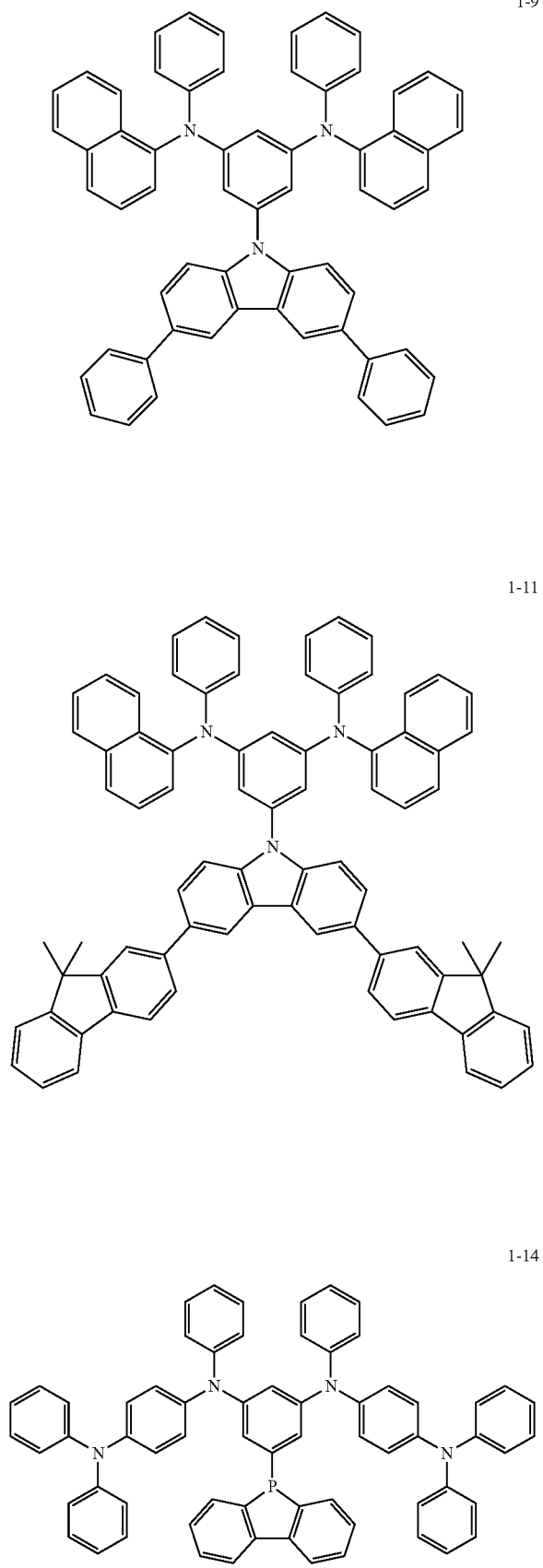
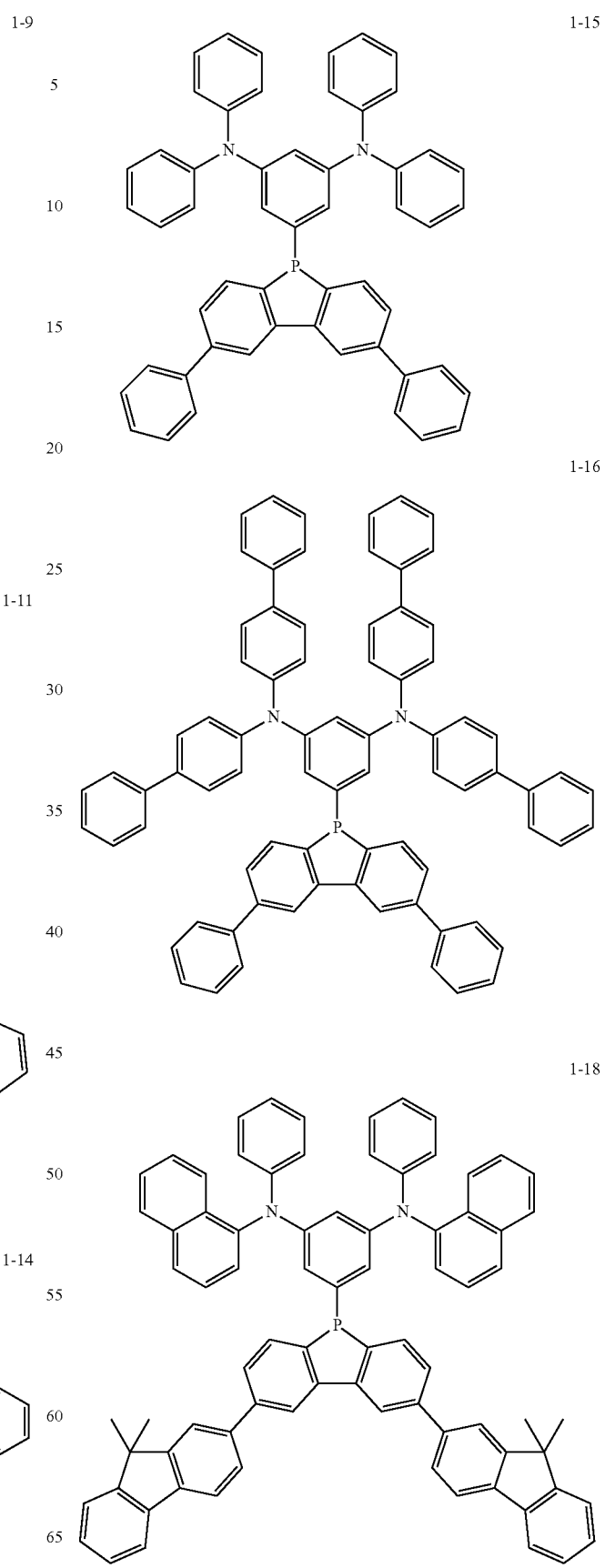

-continued 1-19

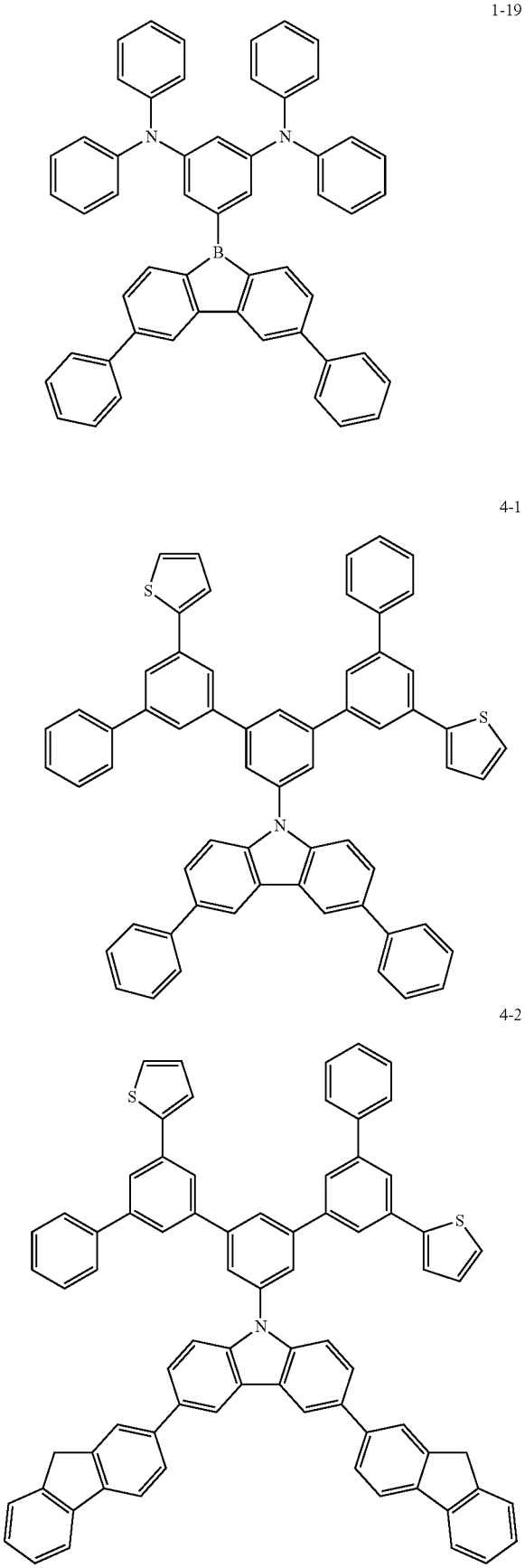

4-1

4-2

-continued

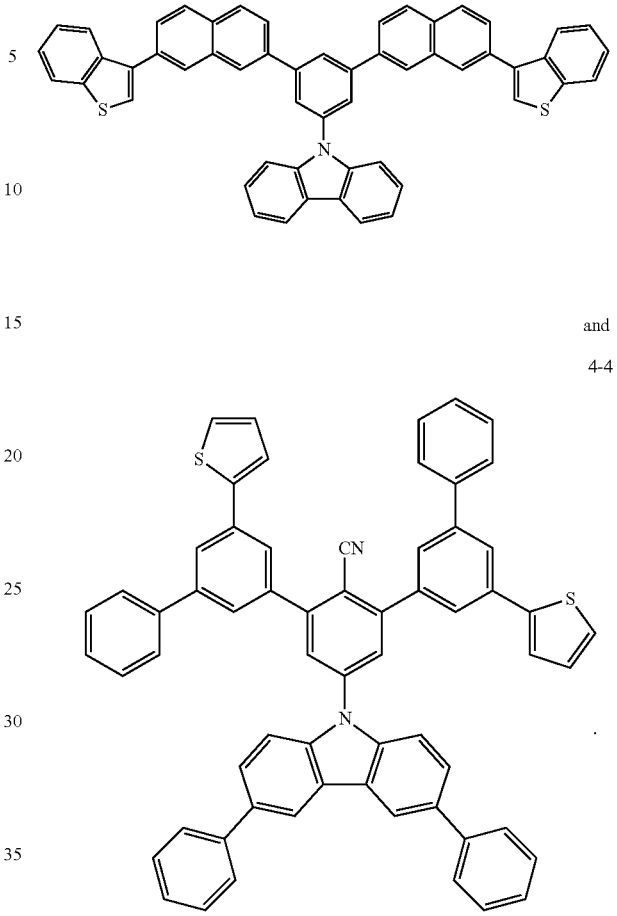

4-3 and 4-4

2. An organic electronic device (OED) comprising a compound according to claim 1.

3. The OED of claim 2, further comprising:
a first electrode;
a second electrode;
at least one organic layer formed between the first electrode and the second electrode and including an emitting layer; and
a hole transport layer formed between the first electrode and the emitting layer and containing a hole transport material, the hole transport material being the compound according to claim 1.

4. The OED of claim 2, further comprising:
a first electrode;
a second electrode;
at least one organic layer formed between the first electrode and the second electrode and including an emitting layer; and
a hole transport layer formed between the first electrode and the emitting layer and containing a hole transport material and a p-type dopant, the hole transport material being the compound according to claim 1.

5. The OED of claim 4, wherein the p-type dopant includes at least one selected from the group consisting of a p-type organic dopant and a p-type inorganic dopant.

6. The OED of claim 4, wherein the hole transport layer is doped with the p-type dopant in an amount of 0.5 to 20 parts by weight with respect to 100 parts by weight of the hole transport material.

7. The OED of claim 2, further comprising:
a first electrode;
a first hole transport layer containing a hole transport material and a p-type dopant;
a second hole transport layer containing a hole transport material;
at least one organic layer including an emitting layer; and
a second electrode; are sequentially stacked,
wherein the hole transport materials contained in the first and second hole transport layers being each independently the compound according to claim 1.

8. The OED of claim 7, wherein the first hole transport layer has a thickness of 800 to 1500 Å, and
the second hole transport layer has a thickness of 250 to 450 Å.

9. The OED of claim 7, wherein the second hole transport layer further contains a p-type dopant, and
the content (P1) of the p-type dopant doping the first hole transport layer and the content (P2) of the p-type dopant doping the second hole transport layer satisfy Equation 1:

$$P1/P2 \geq 1 \qquad \text{[Equation 1]}$$

where P1 is the content of a doped p-type dopant with respect to 100 parts by weight of the hole transport material in the first hole transport layer, and P2 is the content of a doped p-type dopant with respect to 100 parts by weight of the hole transport material in the second hole transport layer.

10. The OED of claim 3, further comprising:
at least one of a first blocking layer formed between the first electrode and the emitting layer; and
a second blocking layer formed between the second electrode and the emitting layer,
wherein the first blocking layer and the second blocking layer are each in contact with the emitting layer.

11. The OED of claim 10, wherein the thicknesses of the first and second blocking layers are each independently 10 to 200 Å.

12. An electronic system comprising the OED of claim 2.

13. The electronic system of claim 12, which is a display device or a lighting device.

* * * * *